United States Patent
Johns et al.

(10) Patent No.: US 7,673,496 B2
(45) Date of Patent: Mar. 9, 2010

(54) DEVICE FOR MEASURING BACK PRESSURE IN CHEMICAL REACTOR TUBES

(75) Inventors: Clifford L. Johns, Louisville, KY (US); Daniel D. Sympson, Louisville, KY (US)

(73) Assignee: Tubemaster Inc, Louisville, KY (US)

( * ) Notice: Subject to any disclaimer, the term of this patent is extended or adjusted under 35 U.S.C. 154(b) by 1 day.

(21) Appl. No.: 12/201,278

(22) Filed: Aug. 29, 2008

(65) Prior Publication Data

US 2008/0314119 A1 Dec. 25, 2008

Related U.S. Application Data

(60) Division of application No. 11/244,450, filed on Oct. 6, 2005, which is a division of application No. 10/800,490, filed on Mar. 15, 2004, now Pat. No. 6,981,404, which is a continuation-in-part of application No. 10/097,908, filed on Mar. 14, 2002, now Pat. No. 6,725,706.

(60) Provisional application No. 60/276,780, filed on Mar. 16, 2001, provisional application No. 60/314,859, filed on Aug. 24, 2001.

(51) Int. Cl.
G01M 3/02 (2006.01)
G21C 17/017 (2006.01)

(52) U.S. Cl. ................ 73/37; 73/49.5; 73/40; 73/49.6; 376/247; 376/249; 702/140

(58) Field of Classification Search .............. 73/37, 73/40, 49.5, 49.6, 700, 714, 756, 861.41, 73/861.44; 702/140; 376/245, 247, 249, 376/250

See application file for complete search history.

(56) References Cited

U.S. PATENT DOCUMENTS

| 3,916,960 | A | 11/1975 | Thompson |
| 3,919,880 | A | 11/1975 | Seyd et al. |
| 4,402,643 | A | 9/1983 | Lytton et al. |
| 4,461,327 | A | 7/1984 | Magin et al. |
| 4,799,377 | A | 1/1989 | Strong et al. |
| 5,293,771 | A | 3/1994 | Ridenour |
| 5,890,868 | A | 4/1999 | Comardo |
| 6,694,802 | B1 | 2/2004 | Comardo |
| 6,981,422 | B1 * | 1/2006 | Comardo ............ 73/756 |

FOREIGN PATENT DOCUMENTS

| DE | 39 35 636 | 5/1991 |
| JP | 47-13043 | 4/1972 |
| JP | 07 256082 | 2/1996 |
| JP | 10-240896 | 9/1998 |

OTHER PUBLICATIONS

Gulf Catalyst—DP Tester—May 14, 1999 (Author Unknown).*
Tubular Reactor Technology brochure, Catalyst Technology, Inc., Buckner, KY 40010 US (prior to 2002).
An offer for sale of a computerized pressure test system by VESCO in 1995.
"Tube Sheet Diagram for Windows" D.H. Breeze, Inspection Software Limited, Insight vol. 36, No. 6, Jun. 1994.

* cited by examiner

*Primary Examiner*—Daniel S Larkin
(74) *Attorney, Agent, or Firm*—Camoriano and Associates; Theresa Fritz Camoriano

(57) ABSTRACT

A device and method for measuring the back pressure in chemical reactor tubes includes many automated features. Inflatable tube seals may be automatically inflated. The device may measure several tubes at once. It may transmit data electronically to a remote computer for analysis and graphic display.

5 Claims, 24 Drawing Sheets

Tube Pressure Analysis

| Condition | | Load Method | |
|---|---|---|---|
| n m.  | | name  | |

| | Pressure | Tubes | K$ |
|---|---|---|---|
| High | value  | value  | $ |
| Low | value  | value  | $ |
| Plugged | value  | value  | $ |
| Open | value  | value  | $ |

Tube In-Criteria Analysis

| | Tubes | % |
|---|---|---|
| Tubes In-Crit. 1st Test | value | value |
| Tubes In-Crit. 2nd Test | value | value |
| Tubes In-Crit. nth Test  | value | value |

DEVICE FOR MEASURING BACK PRESSURE IN CHEMICAL REACTOR TUBES

This application is a divisional of U.S. patent application Ser. No. 11/244,450, filed Oct. 6, 2005, which is a divisional of U.S. Pat. No. 6,981,404, filed Mar. 15, 2004, which is a continuation-in-part of U.S. Pat. No. 6,725,706, filed Mar. 14, 2002, and claims priority from and incorporates by reference U.S. Provisional application Ser. No. 60/276,780, filed Mar. 16, 2001 and U.S. Provisional application Ser. No. 60/314, 859, filed Aug. 24, 2001.

BACKGROUND

The present invention relates to tubes in chemical reactors, and, in particular, devices and methods for measuring the back pressure in the tubes and for blowing dust out of the tubes.

Many chemical reactors use a catalyst as part of the reaction process. The catalyst material frequently is coated onto or contained in a substrate which is packed in tubes within the reactor. The reactants flow through the tubes and out the open ends of the tubes, reacting in the presence of the catalyst to form the products of the reaction. It is desirable to be able to measure the packing of catalyst within the tube in order to determine whether the tube will function properly. Ideally, the catalyst packing in all the tubes will be very close to the same. However, in reality, there is a variation in packings which adversely affects the efficiency of the reaction by providing for different residence times in different tubes.

In order to assess the catalyst packing, a constant flow rate test gas is injected into the tubes, and the back pressure is measured, with the back pressure being proportional to the packing density. Higher densities produce higher back pressures, and lower densities produce lower back pressures. High back pressures can also indicate problems other than high packing density, such as dust, fines, obstructions in tubes, and the presence of foreign material. Low back pressures can also indicate problems other than low packing density, such as bridging. The goal is to measure the back pressure on each tube and determine which tubes require corrective action. Then, once the appropriate corrective action has been taken, the corrected tubes can be retested.

Measurements may be taken when the tubes are first loaded with catalyst, in order to ensure that they are properly loaded, as well as periodically during the operation of the reactor, such as during normal maintenance shut-downs, and after cleaning. However, the devices and methods that have been used in the past have been labor intensive and time consuming, their accuracy has depended largely upon the skill of the operator, and they have yielded data that is not readily usable.

In order to obtain a seal between the test device and the chemical reactor tube, the operator has typically inserted a stopper into the tube. Weldments and obstructions at the top of the tube can interfere with the ability to obtain a good seal, and failure of the operator to maintain the device in a vertical orientation may also interfere with the ability to obtain a good seal. The operator typically must keep track of his position manually, and the data that is obtained is typically written down on a notepad by a second person, sometimes with the person who takes the measurements shouting over the noise of the plant to the person writing down the results. Also, the tubes are typically measured one at a time, requiring many workers and a long shut-down time. With typical prior art methods, it is difficult to keep track of all the measurements, since there may be as many as 35,000 tubes to be measured in a reactor, and transferring data from the many notepads is slow and provides an opportunity for errors. In order to display the progress of the measurement process, the operators usually put colored caps on the tubes as they are measured, which is time-consuming.

SUMMARY OF THE INVENTION

The present invention provides a device and method that improves the ability to measure the back pressure in tubes, making the process much more accurate, faster, less labor intensive, more efficient, safer, less dependent on the skill of the worker, and yielding more accurate and more useful results. In a preferred embodiment, the measuring device uses an inflatable, conforming seal, which provides a good seal between the measuring device and the chemical reactor tubes, even when weldments or other obstructions are present. Also, in a preferred embodiment, the measuring device measures multiple tubes at once rather than measuring only one tube at a time. Also, in a preferred embodiment, measurements are stored at the measuring device, are transmitted electronically to a remote computer, and are displayed graphically in real time at a remote display, such as in the control room, including indications of which tubes are within predetermined specifications and which are not.

The visual display helps the plant engineer determine which tubes require corrective action and may permit the elimination of the time-consuming prior art process of putting caps on all the tubes as the measurements are being taken.

Preferred embodiments of the present invention also permit automated handling of the data and prompt statistical analysis and cost-effectiveness analysis of the measurement data in order to help the plant engineer make quick decisions about corrective actions to be taken. The measurements that have been taken with a prototype device made in accordance with the present invention are so accurate that the engineers can begin to recognize what particular variations in pressure drops mean—for example, one pressure drop indicates that a foam pig accidentally has been left in the tube after cleaning, while another indicates that an extra clip has been inserted to retain the catalyst. In addition, in a preferred embodiment of the invention, a device and method are provided to remove dust from the tubes by blowing gas through them.

The gas used in the preferred embodiments as described herein may be air, nitrogen, or some other gas.

DESCRIPTION OF THE PREFERRED EMBODIMENTS

Figure 1:
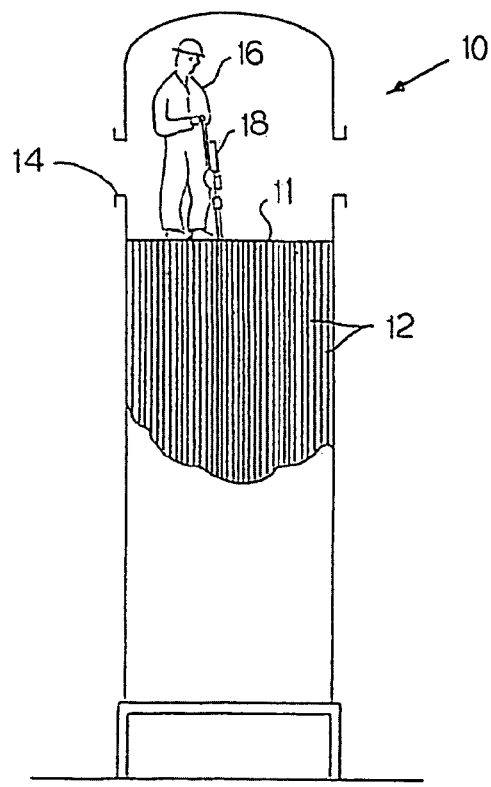
FIG. 1 is a schematic front view, partially in section, of a chemical reactor including tubes packed with catalyst, and including a worker measuring the back pressure in the tubes in accordance with the present invention.

FIG. 1 is a schematic view of a chemical reactor 10, including a plurality of tubes 12, which hold catalyst. The tubes 12 extend downwardly from an upper plate (or tube sheet) 11 and are open on the bottom, except for clips (not shown), which may be used to prevent the catalyst from falling out the bottom of the tubes. A manway 14 provides access for workers to get into the reactor 10. A worker 16 is shown inside the reactor 10, measuring the back pressure in the catalyst tubes 12. In other reactors, the top may be fully removable, providing improved access.

Figure 2:
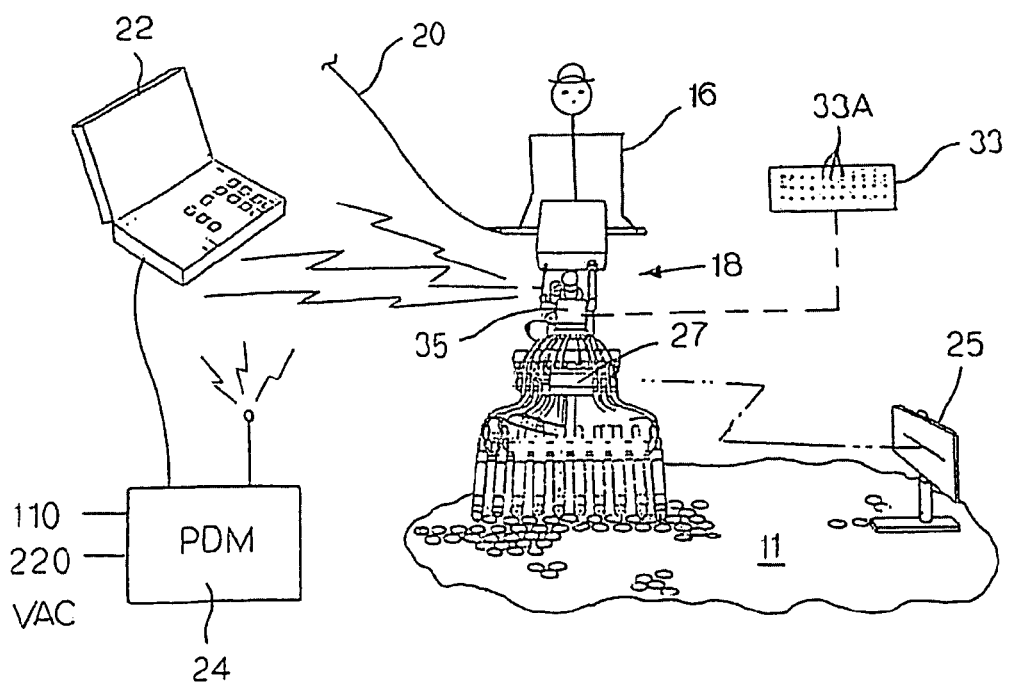
FIG. 2 is a schematic view of a worker measuring the back pressure of the tubes in accordance with the present invention.

FIG. 2 shows the worker 16 standing on the plate 11 and operating a hand-held wand 18, which measures the back pressure in the tubes 12. The details of the wand 18 are shown better in FIG. 4. The wand includes a handle 28, a wand body 26, and a plurality of injector tubes 30 rigidly mounted together to form a single portable unit which is sufficiently rigid that the injector tubes can be inserted simultaneously into their respective reactor tubes simply by picking up the wand 18 by the handle 28, aligning the wand 18 with the group of reactor tubes to be measured, and then lowering the wand's handle 28 so that all the injector tubes 30 enter into respective reactor tubes 12 at once. When the wand 18 is inserted into a bank of ten tubes in the plate 11, it is self-supporting and rests on the plate 11. The wand 18 is connected to a gas line 20 and communicates with a remote computer 22 through a power and data module 24. In this particular embodiment, the gas line 20 is the plant air supply. The power and data module 24 may supply the power to the computer 22 and to the hand-held wand 18. However, the wand 18 preferably operates on battery power, and the computer 22 preferably operates on a battery or is plugged into a regular alternating current outlet. The wand 18 communicates with the power and data module 24 in real time by means of radio signals, but other means for transmitting data to the computer 22 could be used, such as hard wiring the wand 18 to the power and data module 24 or downloading data from the wand 18 onto a portable medium such as a disk, which can then be carried to the remote computer 22. The remote computer 22 may be located in the control room or in some other convenient location.

Also shown in FIG. 2 is a target 25, which is used by a laser measuring device 27 on the wand 18 to determine the position of the wand 18 in order to confirm which tubes 12 are being measured. The target 25 preferably is placed in the first tube 12 of a row, and serves as a reference point, as will be described later. While the target 25 has proven to be a convenient reference point for making measurements, other reference points could be used, such as the side wall of the reactor, for example.

Figure 4:
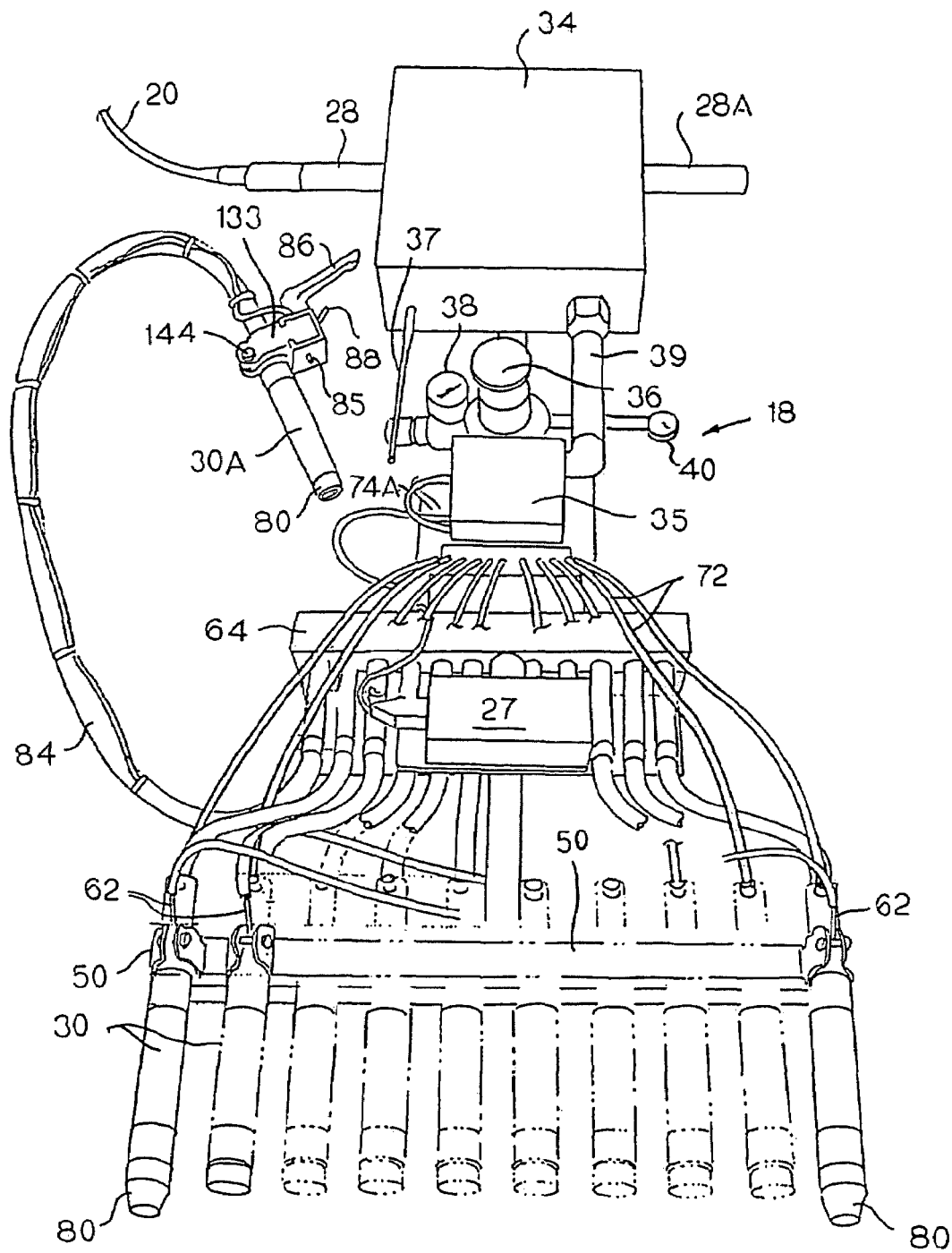
FIG. 4 is a schematic front perspective view of a device for measuring the back pressure of tubes, made in accordance with the present invention.

The location of the laser measurement device 27 is best seen in FIG. 4. FIG. 4 shows that the laser measuring device 27 is fixed relative to the injector tubes 30 by being affixed to the wand. As a result, the distance measured by the laser to the reference point also establishes the position of each of the injector tubes 30 relative to the reference point. Thus, when the injector tubes 30 are placed in their respective receptacles, the reactor tubes 12 can be identified automatically based on the distance measured by the laser. So the injector tubes 30 are not only used to inject fluid but also function as probes which locate the tube positions.

Figure 3:
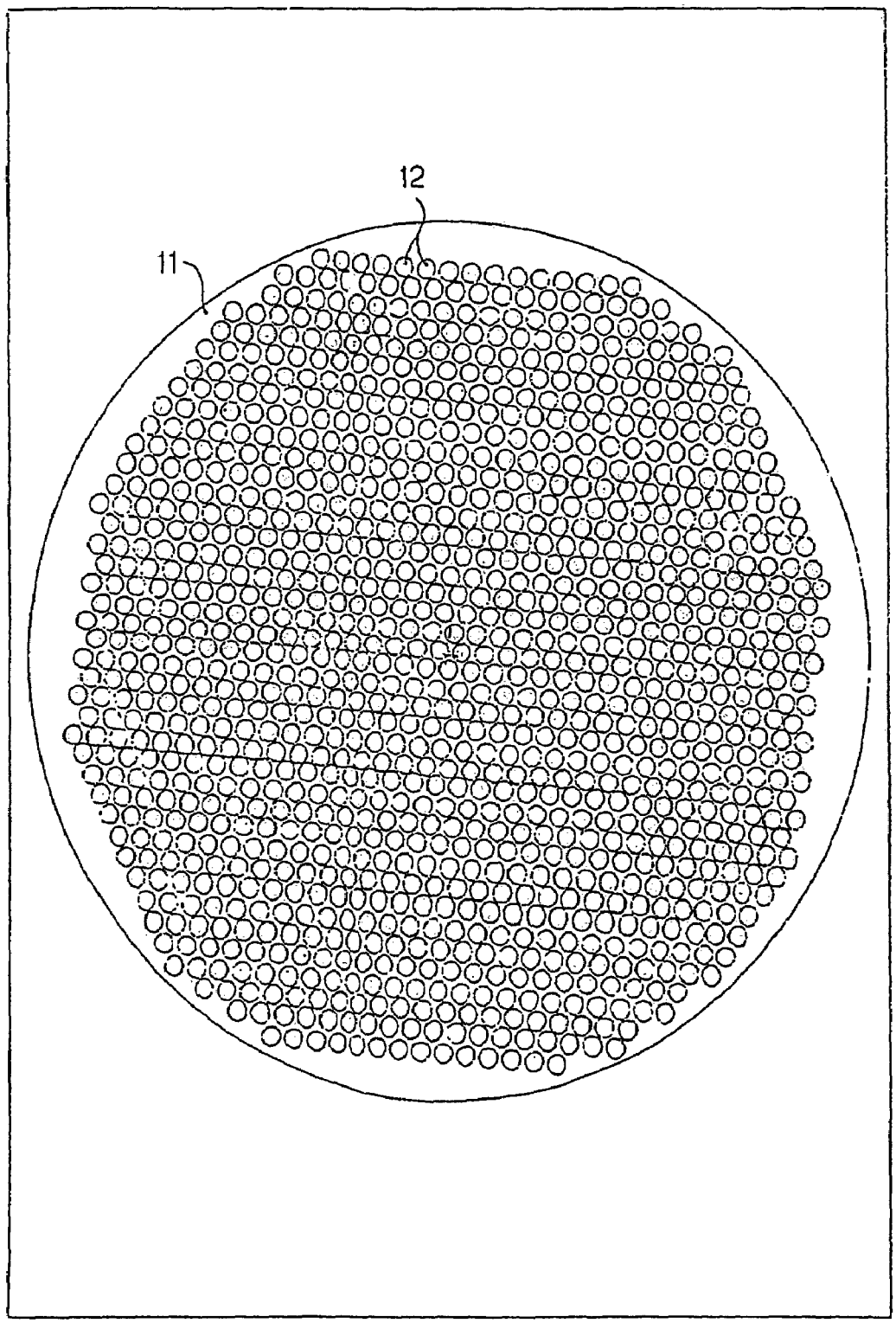
FIG. 3 is a plan view of a tube layout for the reactor being measured, which is displayed on a graphic display as the measurements are being made.
Figure 12:
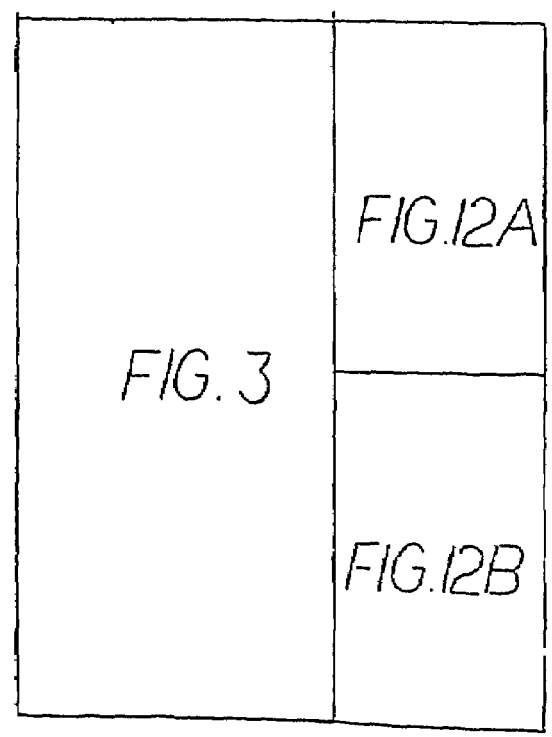
FIG. 12 is a schematic view of the graphic display shown at the remote, computer in the arrangement of FIG. 2.

FIG. 3 is a plan view of the plate 11. This plan view is also a portion of the screen display that is shown on the display screen of the computer 22 to visually indicate the tubes that are being measured, as shown in FIG. 12. Prior to using the wand 18 in the reactor 10, a layout of the tubes is obtained and is made available to the computer 22 and to the controller 32 for the wand 18. This layout is shown graphically as in FIG. 3. As the wand 18 is being used, the data from the wand 18 is stored at the wand 18 and is transmitted to the computer 22. This data is displayed on the screen of the computer 22 or other graphic interface, as will be explained later.

FIG. 4 is a front schematic view of the wand 18. The wand 18 includes a hollow wand body 26 (see FIG. 5), with a hollow handle 28 at its upper end and a plurality of injector tubes 30 at its lower end. The wand 18 receives regulated pressurized gas (such as air, nitrogen, or another gas) through a gas line 20. The wand 18 defines two different gas paths for each injector tube 30a test gas path and an inflation gas path. The test gas path provides the gas that passes through the injector tube 30 into the respective chemical reactor tube 12 for testing the chemical reactor tube. The inflation gas path provides the gas that is used to inflate the seal on the injector tube 30 so that the injector tubes 30 of the wand 18 seal against the interior of the respective chemical reactor tubes 12.

Figure 9:
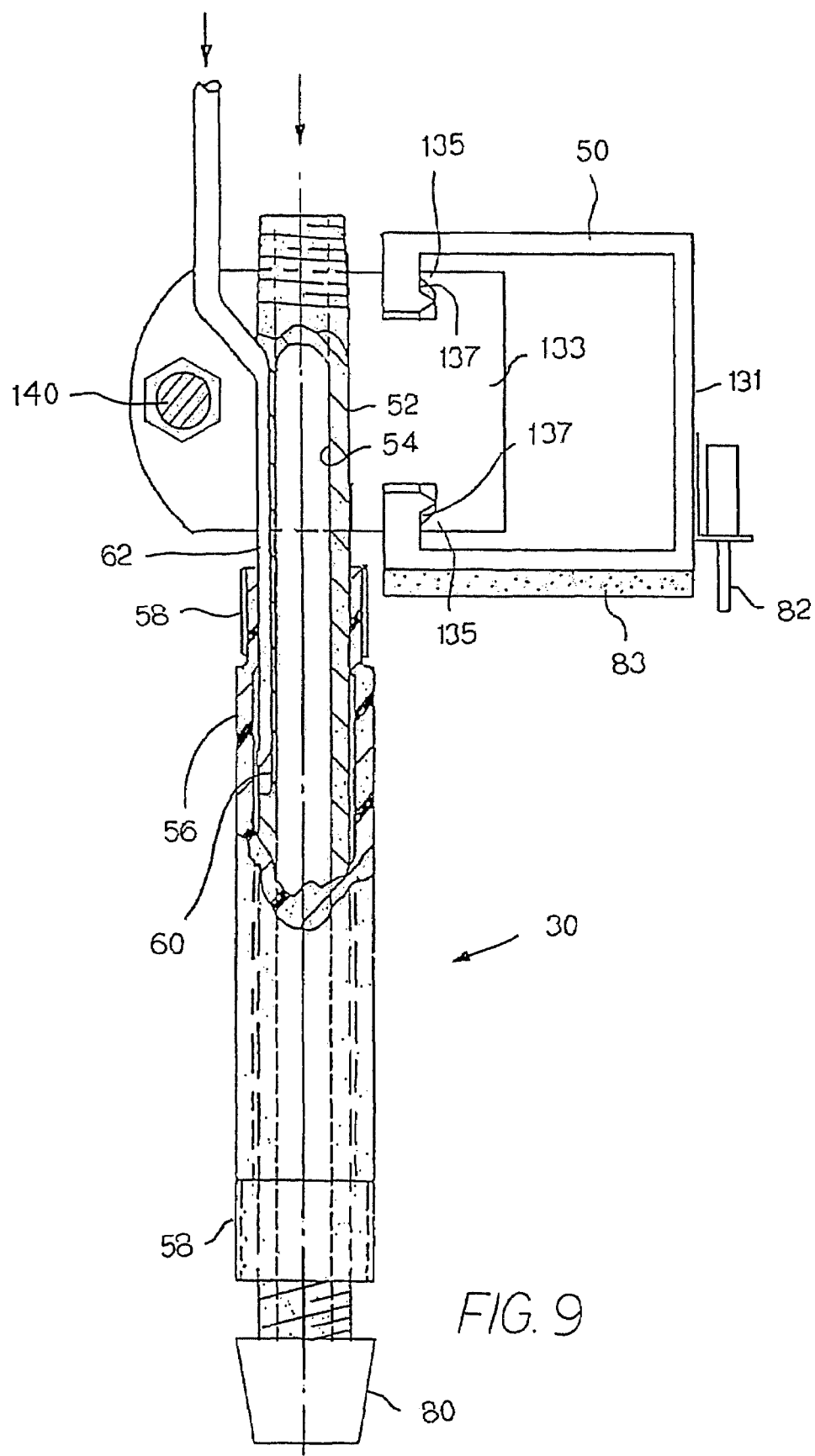
FIG. 9 is a side view partially in section showing one of the injector tubes of the device of FIG. 4.
Figure 10:
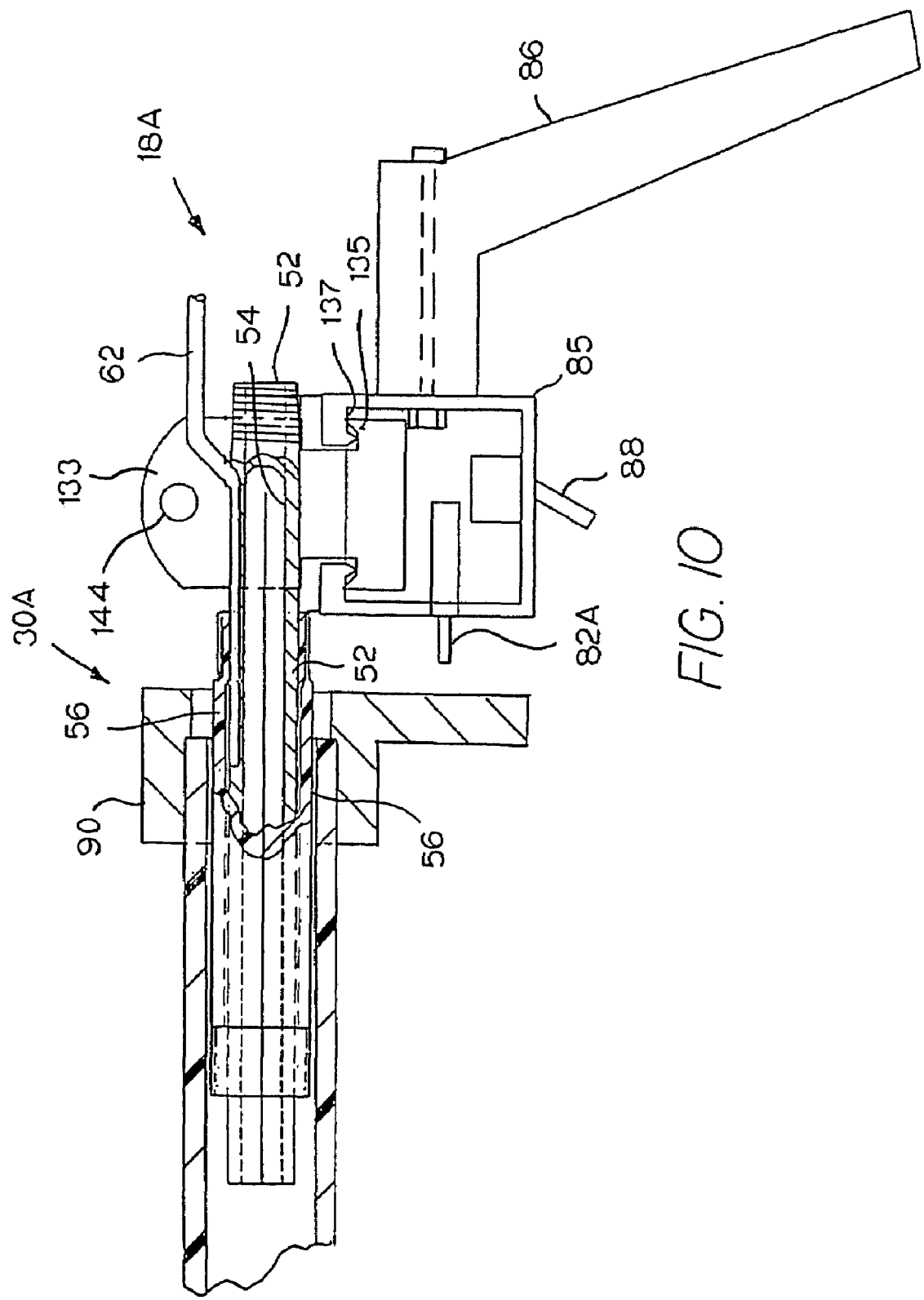
FIG. 10 is a side view partially in section of the umbilical wand portion of the device of FIG. 4.

As shown in FIG. 9, each of the injector tubes 30 includes a hollow tubular member 52 defining an internal gas flow path 54 with an open bottom outlet through which the test gas passes into the respective chemical reactor tube 12. A gas-impermeable, elastic sleeve 56 is mounted over the tubular member 52 and is sealed against the tubular member 52 by means of upper and lower ferrules or clamps 58. A recess 60 is formed in the outer surface of the tubular member, and that recess 60 receives an inflation tube 62. The depth of the recess 60 preferably is the same as the thickness of the inflation tube 62 at the upper ferrule or clamp 58, so that a good seal is formed there. The inflation tube 62 forms an inflation gas path that allows gas to be injected between the outer surface of the tubular member 52 and the inner surface of the sleeve 56 in order to inflate the sleeve 56. The inflation tube 62 preferably is welded, adhered, or otherwise secured to the tubular member 52. The bottom of the tubular member 52 is threaded, and this particular tubular member 52 receives a frustro-conical guide member 80 on its threaded end, which helps guide the injector tube 30 into the chemical reactor tube 12.

FIGS. 4-10 show the main components of the wand 18. Mounted on the wand 18 is a main wand control box 34, which houses the main controls for the wand 18. An antenna 37 projects out of the control box 34. Below the main wand control box 34 is a secondary control box 35. A conduit 39 houses wires and a measuring tube 74A that extend between the control boxes 34, 35. A manual shut-off valve 36 can be used to shut off the flow of gas through the wand body 26. An inflation gas pressure regulator 38 regulates the pressure of gas going to the inflation tubes 62. An inflation path solenoid valve 42 (see FIG. 8) opens and closes the gas flow to the inflation tubes 62. An inflation path manifold 44 (see FIG. 7) distributes the incoming inflation gas to a plurality of hose fittings 46, which connect to hoses 48, which lead to the inflation gas paths 62 of the injector tubes 30.

Figure 21:
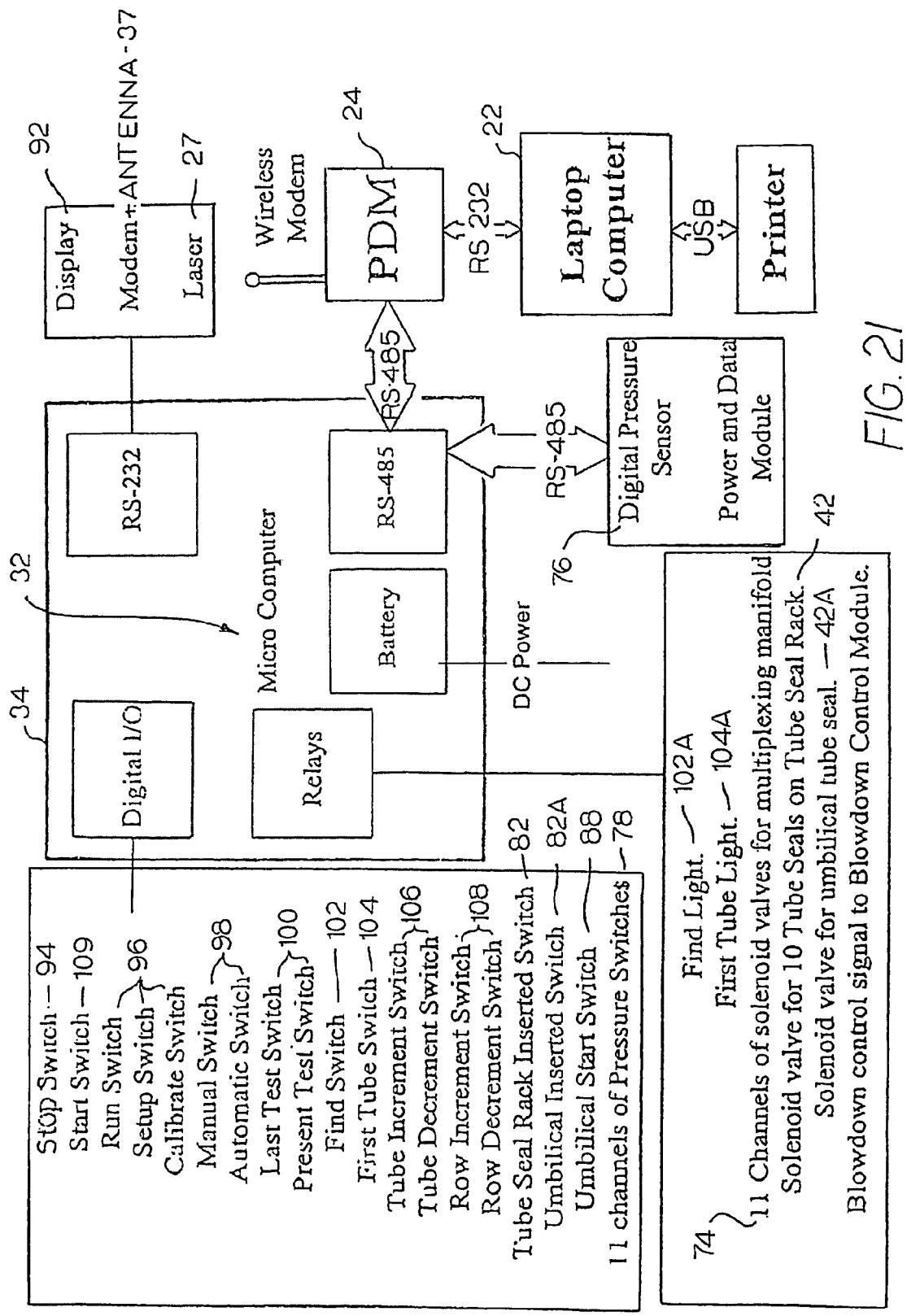
FIG. 21 is an electrical schematic of the device of FIG. 4.

In this particular embodiment, there are eleven injector tubes—ten injector tubes 30 mounted on a frame member 50, and the eleventh injector tube 30A is on a freely-movable umbilical wand 18A, generally for use in locations that are not accessible by the larger wand 18. The umbilical wand 18A can be used independently of the ten other injector tubes 30, so the ten tubes 30 can be inserted into reactor tubes when the umbilical wand 18A is in use, or they can be completely out of the reactor tubes when the umbilical wand 18A is in use. There is a cushion 83 on the bottom of the frame member 50 to help absorb the impact as the injector tubes 30 of the wand 18 are inserted into the chemical reactor tubes 12. It is preferred that a separate inflation path solenoid valve 42A be provided for the umbilical seal 30A, as shown in the schematic of FIG. 21.

Figure 8:
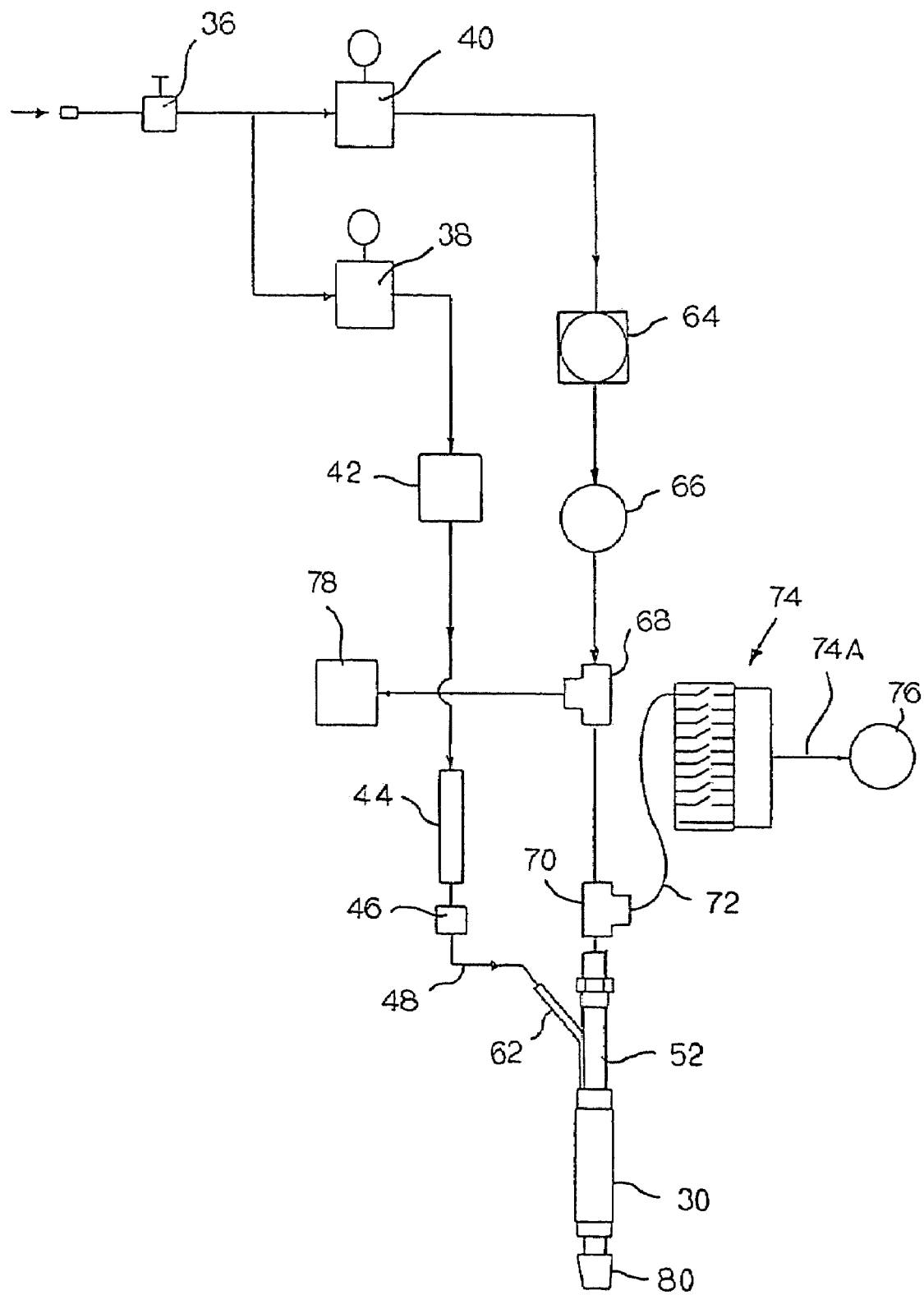
FIG. 8 is a schematic gas flow diagram for the device of FIG. 4.

Referring to FIG. 8, the test gas passes through the shut-off valve 36, through the main pressure regulator 40, and to the main manifold 64, which distributes the test gas to a plurality of needle valves or other constant flow devices 66, such as sonic nozzles, orifice plates, or precision orifices. A Nozzle or orifice can be used to obtain and maintain a constant gas flow rate while back pressure testing. Back pressure testing may be used for various purposes, such as to verify that the packing density of catalyst is proper or to determine, that a tube is empty after it has been cleaned. Tubes can be difficult to completely clean along their entire length and are typically cleaned by water blasting, sand blasting, passing a compliant material through them such as a piece of foam propelled by compressed air, or by wire brushing or passing a wire brush along the tube length using compressed air. Constant gas flow of the test gas is achieved by operating each nozzle or orifice in such a manner that its sonic coefficient is maintained. A sonic condition is said to be achieved and maintained if the ratio of downstream absolute pressure to upstream absolute pressure through the nozzle or orifice is less than its sonic coefficient. Then the flow through the nozzle or orifice should be sonic and should provide a constant flow rate. This permits the back pressure measurement to be used to indicate the degree of obstruction, from an open tube, to a tube packed with catalyst, up to a certain maximum back pressure at which the sonic coefficient is no longer satisfied. The flow rate is accordingly designed to ensure that the regulator mounted on the wand body, its adjusted setting, and the orifice or nozzle opening are all coordinated for a specific flow rate through the tube under test up to a maximum back pressure. From each constant flow device 66, the test gas passes through a respective T 68, and through the internal path 54 of the respective tubular member 52 into the respective chemical reactor tube 12. Another T fitting 70 is located just above each tubular member 52, and a measurement tube 72 extends from each fitting 70 to its respective inlet at the multiplex manifold at the multiplex valve 74. The outlet of the multiplex valve 74 is connected to a pressure sensor 76. A pressure switch 78 is in communication with each measurement tube 72, and, if the pressure in the line exceeds a predetermined limit, the pressure switch 78 closes and prevents the channel of the multiplex valve 74 corresponding to that measurement tube 72 from opening, thereby preventing gas communication with the digital pressure sensor 76. This protects the pressure sensor 76 from being damaged by exposure to high pressure gas.

When the wand 18 is being used to test a plurality of chemical reactor tubes 12, the test gas flows continuously through the tubular members 52 into the chemical reactor tubes 12, and the multiplex valve 74 goes through a cycle by which it puts each of the measurement tubes 72 in gas communication with the pressure sensor 76, one at a time. In this manner, a single pressure sensor 76 is used to measure the back pressure in all the injector tubes 30 of the wand 18. Since the gas flow entering the chemical reactor tubes 12 through the injector tubes 30 has been carefully regulated by the flow control devices 66 to establish a pressure drop across the flow control devices 66 and a constant gas flow to the tubes 12, the back pressure that is generated in each chemical reactor tube 12 is in proportion to the flow resistance produced by the catalyst in that chemical reactor tube 12. That resistance, in turn, is proportional to the density with which the catalyst is packed (which is to be assessed by the testing operation). As the chemical reactor tube 12 becomes more and more packed, the back pressure approaches the pressure on the supply side of the flow control device 66.

It will be noted that at least the injector tubes 30 at the ends of the wand 18 and on the umbilical injector tube 30A have tapered end pieces 80, which help in guiding the wand 18 into the chemical reactor tubes 12 to be tested. Of course, tapered ends 80 could be provided for all the injector tubes 30 if desired. In this embodiment; the injector tubes 30 are arranged; linearly, with an equal spacing between the injector tubes 30. However, other arrangements, such as a triangular array of injector tubes 30 could be provided if desired. The spacing between the injector tubes 30 can be adjusted, and different diameter injector tubes 30 may be used, depending upon the configuration of the reactor, as will be described later.

There is an interlock switch 82 on an adjustable position clip (see FIG. 5) which projects downwardly from behind the frame member 50. The purpose of the switch 82 is to ensure that the injector tubes 30 are inserted all the way into the chemical reactor tubes 12, and the switch 82 is contacting the plate 11, before the sleeves 56 can be inflated. When the interlock switch 82 closes, and the start switch 109 is depressed, the central processor 32 causes the inflation path solenoid valve 42 to open and initiates inflation of the sleeves 56. In this embodiment, the switch 82 signals the central processor 32 in the control box 34, which, in turn, closes a relay which opens the inflation path solenoid valve 42, allowing gas to pass through the inflation path manifold 44 to inflate the injector tubes 30. The switch 82 protects the sleeves or bladders 56 against overinflation by preventing them from inflating unless they are inside the chemical reactor tubes 12 to be tested.

Figure 5:
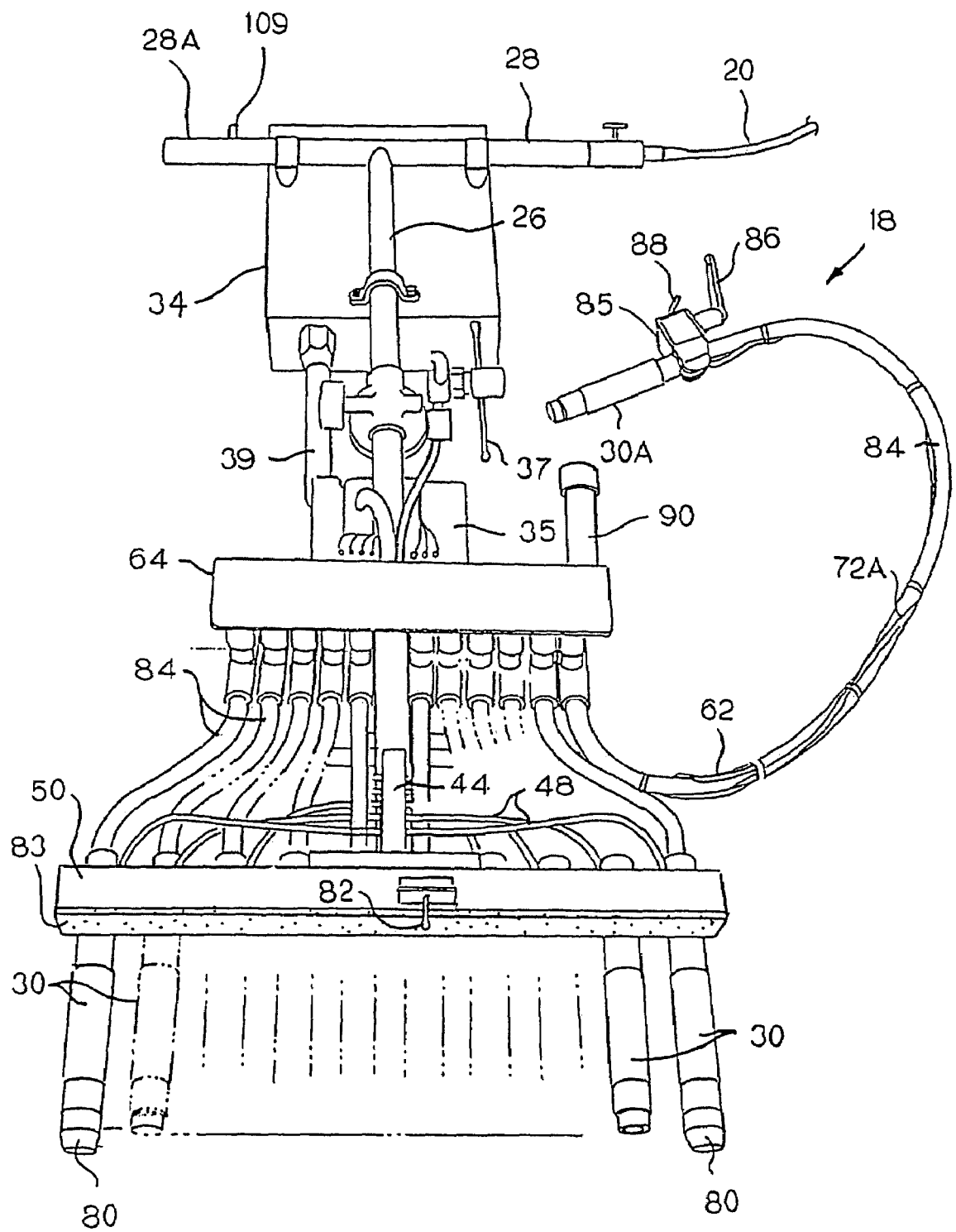
FIG. 5 is a rear view of the device of FIG. 4.
Figure 6:
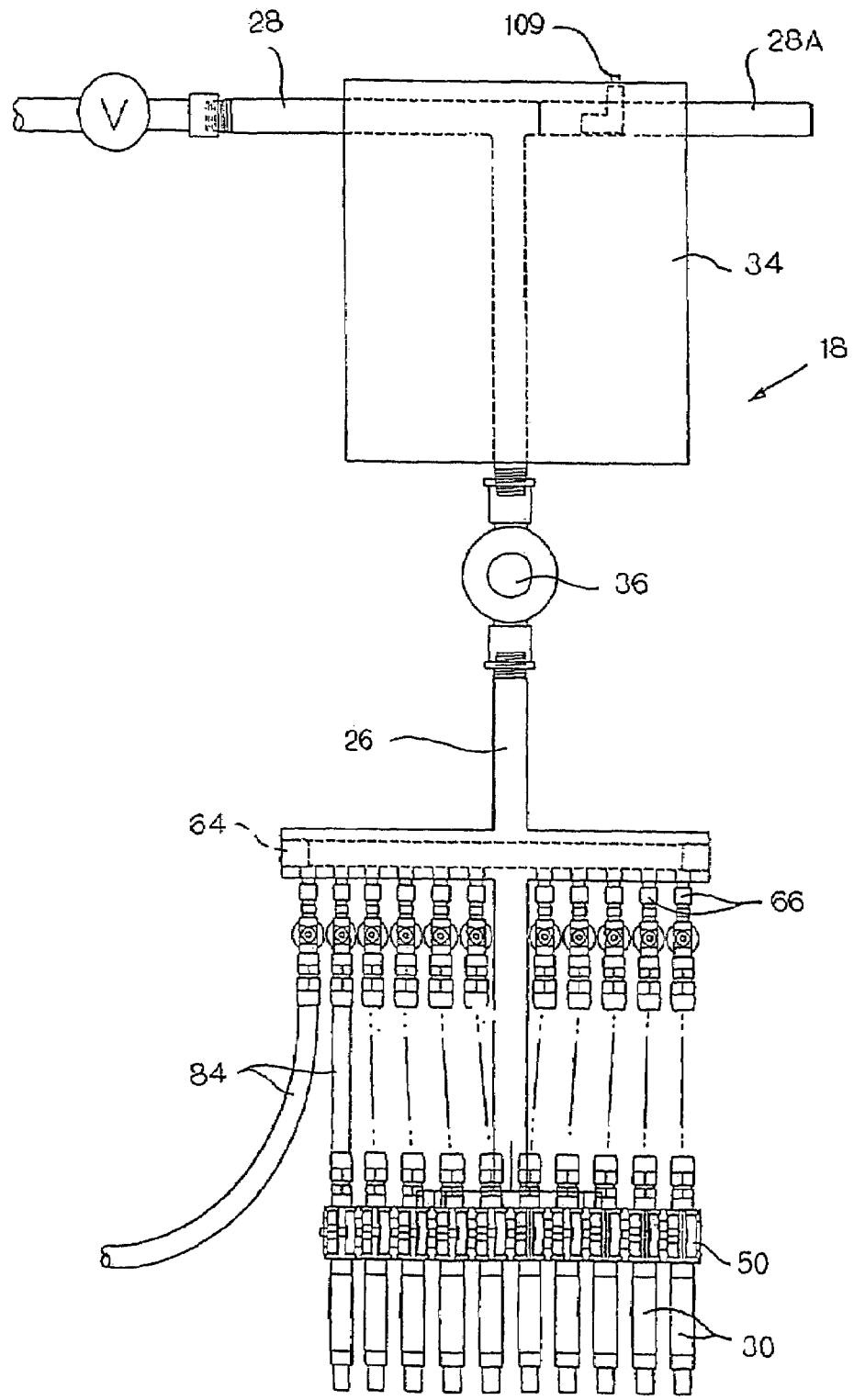
FIG. 6 is a schematic front view of the device of FIG. 4, with some parts removed for clarity.
Figure 7:
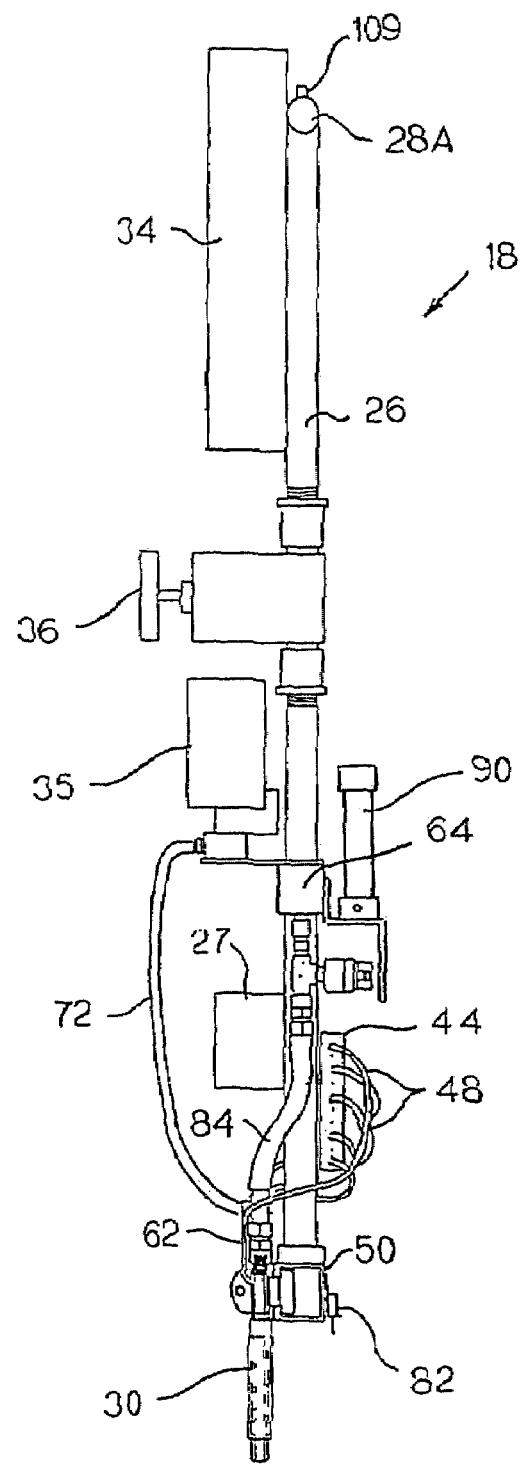
FIG. 7 is a schematic side view of the device of FIG. 4.

The umbilical injector wand 18A (shown best in FIG. 10) includes an injector tube 30A that is essentially the same as the other ten injector tubes 30, except that it is not fixed onto the main frame 50. Instead, as shown in FIG. 5, it is connected to a longer gas inlet hose 84 and has a longer measuring tube 72A and longer inflation tube 62, so that it can be held in the operator's hand and inserted individually into one of the chemical reactor tubes 12. This is helpful in the event that some of the chemical reactor tubes 12 are not accessible by the regular bank of injector tubes 30. The umbilical injector tube 30A also includes a tubular member 52 defining an internal path 54, and a sleeve 56 and an inflation tube 62, which is used to inflate the sleeve 56.

At the top of the body of the umbilical wand 18A is a frame member 85, and a handle 86 is mounted onto the frame member 85. Projecting downwardly from the bottom of the frame member 85 is an interlock switch 82A, which serves the same function as the interlock switch 82 on the main frame 50, ensuring that the umbilical injector tube 30A is inserted into the chemical reactor tube 12 and the switch 82A is depressed against the plate 11 before the solenoid valve 42A is activated so that the sleeve 56 can be inflated. There is also a start switch 88 on the rear surface of the frame member 85, which the operator uses to initiate a test using the umbilical wand 18A. The tubular member 52 of the umbilical injector tube 30A mounts onto its frame member 85 in the same mariner that the other injector tubes 30 mount onto their frame member 50, as will be described later.

A holster 90 (see FIG. 10) mounts on the main wand 18 to hold the umbilical injector tube 30A when the umbilical wand 18A is not in use. When the umbilical injector tube 30A is inside the holster 90, its sleeve 56 is enclosed and contained by the holster 90.

Figure 11:
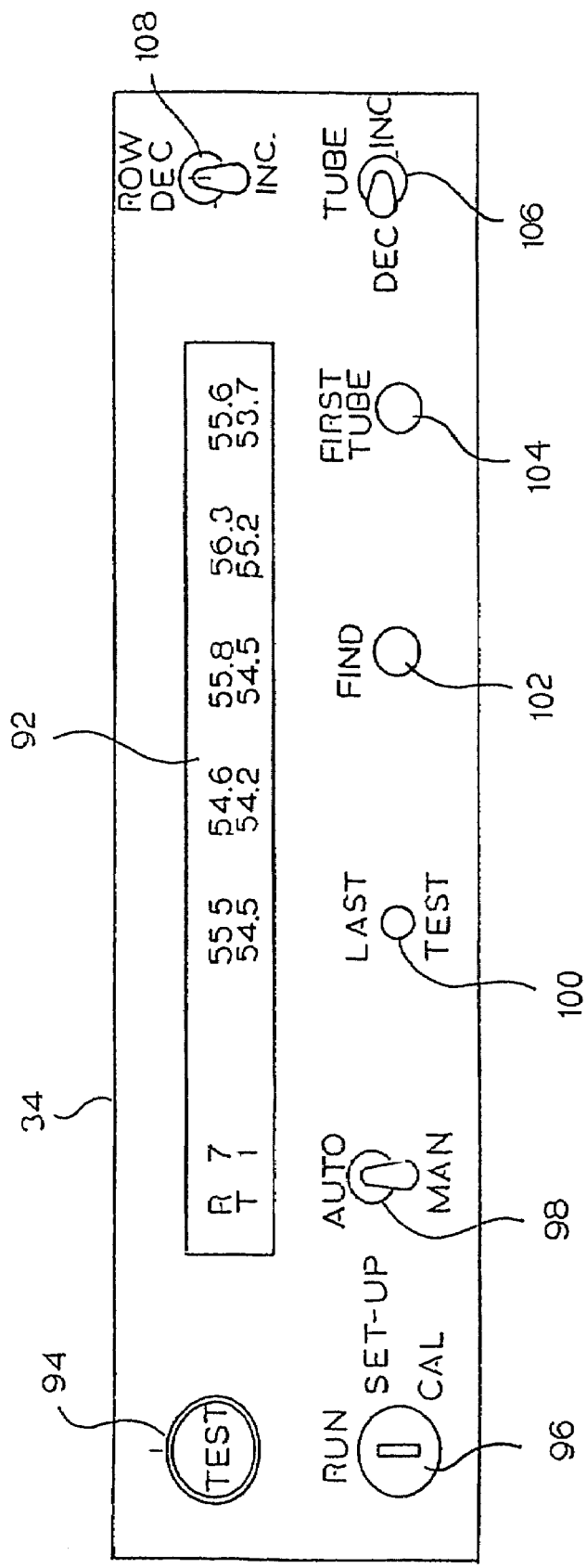
FIG. 11 is a plan view of the control panel of the device of FIG. 4.

FIG. 11 is a view looking down on the control box 34 of the wand 18. The control box 34 includes a display 92 as well as a number of controls, the display 92 in this example is indicating R:7; T:1, which tells the operator that the wand 18 is measuring the chemical reactor tubes 12 in row 7, beginning with tube 1. The display 92 in this view also includes ten pressure readings, which indicate the back pressure in tubes 1-10 of row 7. In the upper left corner is a stop button 94, which can be used to shut off the gas supply to the inflation tubes 62 and stop the measurement. Below that is a keyed switch 96, which is used for initializing and calibrating the unit. Next is a switch 98 that switches the unit between automatic and manual modes. Next is a switch 100 which permits the worker to alternate between viewing the measurements for the current set of chemical reactor tubes 12 and for the previous set of chemical reactor tubes 12. Next is a "find" button 102, which, when pushed, uses the laser measuring device 27 to take a distance measurement relative to the target 25 to determine which group of chemical reactor tubes 12 is being measured. When the "find" button 102 is depressed, it also includes a light 102A, which lights up (see electrical schematic of FIG. 21). Next is a "first tube" button 104, which is depressed to indicate that the wand 18 is at the first tube in the particular row. This button also includes a light 104A (see FIG. 21), which lights up when the button is depressed. Next is a toggle switch 106 for increasing or decreasing the tube number on the display 92, and above that is a toggle switch 108 for increasing or decreasing the row number on the display 92. A "start" button 109 is located on the handle 28A of the wand 18 (see FIGS. 5 and 6), and is depressed by the worker to begin the sequence for measuring a group of chemical reactor tubes 12.

It should be noted that it would be possible to provide devices that include only some of the elements that have been shown here, not requiring all of those elements. For example, it would be possible to provide a device that includes a measurer, such as the laser measurer described above, a couple of probes shaped like the injector tubes 30, that would be inserted into reactor tubes 12, and an on-board computer in which is stored a "list to fix". An operator could then use this device to locate the tubes that were found to need work during the test, for example using the device to locate tubes that need to be capped or marked accordingly for specific corrections such as adding some catalyst or removing the tube contents and refilling with catalyst.

FIGS. 3, 12, 12A, and 12B show an example of the graphic display that is available at the remote laptop computer 22. The data that is input into the laptop 22 and the central processor 32 prior to the test preferably also includes information as to which tube locations actually are taken up by thermocouples or actually house supporting structure or mechanical plugs rather than tubes. If so, this is shown on the screen even before any measurements are taken (as well as afterwards). For example, thermocouples may be shown in orange, while support structure may be shown in black. It should be noted that the modem 24 and computer 22 may be receiving data from several wands 18 at once. The initial layout specifies a row and tube number for every tube position, so that the data that comes in can be associated with a particular position on the stored layout.

As measurements are taken by the wand (or wands) 18, the data, including row and tube number location as well as the back pressure readings and the wand identifier are transmitted electronically back to the modem 24 and are displayed at the computer screen 22 in real time. In this embodiment, the data is transmitted from the antenna 37 on the control box 34 to the antenna on the remote modem 24, but the data could be transmitted through wires, through an internet connection, or through other known transmission means. The data which is stored at the wand 18 could also be downloaded later to the remote computer 22.

The linked data transmitted from the want is graphically displayed in pictorial format at the remote computer 22, as shown in FIGS. 3, 12, 12A, and 12B.

The view of FIG. 3 showing the chemical reactor tubes 12 will indicate the tubes in various colors as they are measured, depending upon whether they have passed the preset criteria for the test. For example, if the tube back pressure measurement is within the specifications for that reactor, then that tube will show up in green on the screen. If the tube fails high, it will show up in red. If it fails low, it will show up in yellow. If the tube back pressure is so high that it is considered plugged, it will show up in dark gray. If the tube back pressure is so low that it is considered open, it will show up in white. Untested tubes show up as a gray ring with a black dot in the center. Of course, this proposed color scheme could be altered by the user if desired, as long as the color usage is consistent. It should also be noted that separate data sets may be kept for various conditions of the reactor, such as for measurements taken after cleaning out the tubes, after filling the tubes, after blowing down the tubes, after operation of the reactor for a period of time, for sample measurements that may be taken to establish the test specifications, and for measurements taken after various corrective actions are taken. Also, these data sets may be stored during the life of the reactor, providing the plant engineer with valuable historic information about the reactor.

The person viewing the computer screen may choose to zoom in on a particular section of the reactor, if desired. If the person viewing the screen wants information about a particular chemical reactor tube 12, he moves his cursor over that tube in the portion of the screen shown in the graphic of FIG. 3, and the information for that tube will appear in the portion of the screen shown in FIG. 12A. For example, the sample shown in FIG. 12A indicates that we are viewing the information for row #12, tube #12. The display indicates the pressure in the most recent test, the status of the tube, the wand 18 which took the measurement, and the date, time, and operator for that measurement. There is also a graphic indicator in the upper right of the screen of FIG. 12A, with rings of color indicating the status of this tube in previous measurements and in the current measurement.

The circle 112 includes an outer band 114, which has a color indicating which wand 18 took the most recent measurement prior to correction. Just inside the outer band 114 is a large color field 116, which indicates by color the results of the most recent test prior to correction. Then there is an inner band 118, which indicates by color which wand took the most recent test after correction. Inside the inner band 118 is another color field 120, which indicates by color the results of the most recent test after correction, and the number 122 inside that field 120 represents the number of times the tube has been retested during the correction process. So, in this case, if the outermost band 114 is blue, that indicates that the blue wand conducted the most recent test prior to making corrections. If the color field 116 just inside the outer band is red, that indicates that the tube failed high on the most recent test prior to correction. If the inner band 118 is also blue, that indicates that the same wand conducted the most recent test during the correction process, and if the small inner color field 120 is green, that indicates that the tube has now passed. The number "2" inside the color field 120 indicates that this tube has been retested twice during the correction process. The original test data are not shown in this icon, but they are stored and can be retrieved as desired. Since the display for any particular tube in FIG. 3 is too small to include all this detail, it will, by default, simply show the color indicating the results of the most recent test. However, if the plant engineer wanted to view the display of FIG. 3 for any historic data set, he could obtain that as well.

Figure 12A:
FIG. 12A shows a portion of the graphic display of FIG. 12.

The portion of the display shown in FIG. 12A also indicates the row and tube, the pressure measured for that tube, the last status as of the previous measurement (if any), the wand number, date, time, and operator for the measurement. Below the data for that particular tube is data about the test in general—the total number of tubes, the number of tubes tested, the percent completed, and statistical information. The plant engineer may access the complete information for any tube simply by pointing to the particular tube on the display of FIG. 3 with the cursor, or he may input the particular tube and row number, or he may run a "list to fix" report or other report, pick up the tubes with problems from that report, and may access the data about those tubes by clicking on them in the report.

Figure 12B:
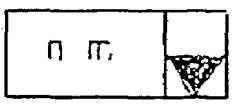
FIG. 12B shows another portion of the graphic display of FIG. 12.
Figure 12B:
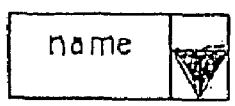
Figure 12B:
Figure 12B:
Figure 12B:
Figure 12B:
Figure 12B:
Figure 12B:
Figure 12B:
Figure 12B:
Figure 12B:
Figure 14:
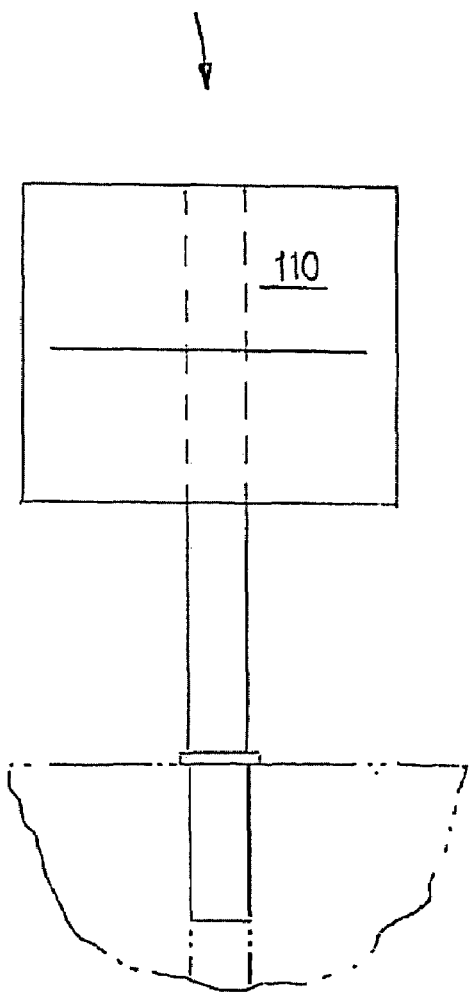
FIG. 14 is a front view of a target for use with the device of FIG. 4.

FIG. 12B shows additional data that is presented on the computer screen. This portion provides the specifications for what pressure would be considered a failure on the high side, what pressure would be considered a failure on the low side, what pressure would indicate that the tube is plugged, and what pressure would indicate that the tube is open. It also indicates how many tubes met those criteria, and what those tubes' failure costs in terms of lost production, wasted reactants, and so forth. There is also an analysis of the number and percentage of tubes that met the criteria for being within the specifications for each test.

In addition to the data shown in these figures, the computer 22 generates a "list to fix", which is a prioritized list of which tubes should be corrected and what should be done to correct them, based on the criteria that have been set, such as cost or pressure criteria.

Of course, once the data has been acquired, the information displayed in these screens can be varied, depending upon what the user wants. For example, the plant engineer may wish to display the "list to fix", indicating in order of priority which chemical reactor tubes 12 should be plugged, which tubes should be blown down, which tubes should be re-loaded with catalyst, and so forth. The plant engineer may set his own criteria, which the computer 22 will use to establish the "list to fix", prioritizing the list based on the criteria that have been established by the plant engineer. The criteria that are established to set the specifications for what is a failure on the high side or the low side and what is "plugged" or "open" may be; specific pressure readings, or they may be based on a statistical analysis of the data. As more data is collected, and as the plant engineer has more experience with the actual pressure data, actual production data, and actual costs, the specifications for determining which tubes pass and which tubes have the highest priority for corrections, and the way the data is used may become much more sophisticated.

The information provided by this arrangement, the speed with which it is delivered, its accuracy, as well as the way it is presented, make it very useful for the plant engineer. The plant engineer now has a way of determining the cost of out-of-specification tubes and the ability to pinpoint them and correct them promptly during the plant shut-down, when time is of the essence. He then can adjust his specification criteria and cost information based on experience. Since the wand reports each tube's measurements back to the computer 22, the plant engineer knows for certain, as the test is being conducted, that the equipment tubes 12 have been tested. This system provides a quality control check on the installers of catalyst. This device and method provide a tremendous amount of useful information in very user friendly format that the plant engineer has never had before. In a variety of ways, it helps the plant engineer make better decisions to improve the efficiency of the plant.

In the prior art, each chemical reactor tube 12 was capped in a certain color as the testing process was proceeding in order to provide a visual indication of the test results and the progress of the test. If desired, a detachable tube capping guide 33 (shown in FIG. 2) may be plugged into the control box 35, including ten rows of lights, with three different colors of lights 33A for each injector tube 30, to indicate by the color of light that is lit up by the central processor 32 whether that tube failed high, failed low, or passed the test criteria. The operator could then use that guide to place the appropriate color of cap onto each tube as the measurements progress. However, it is expected that the visual data provided at the computer 22 will be so much more helpful than were the prior art caps that plant engineers will find the capping step to be unnecessary and will decide to save money by eliminating the use of caps in tests that use the wand 18.

In addition, a simulation package may be provided to the plant engineer prior to taking measurements, to give the plant engineer experience in making decisions about corrective actions to be taken before the measurements are even taken. This may help the plant engineer make quick decisions during the plant shut-down, when time is especially valuable.

Figure 13:
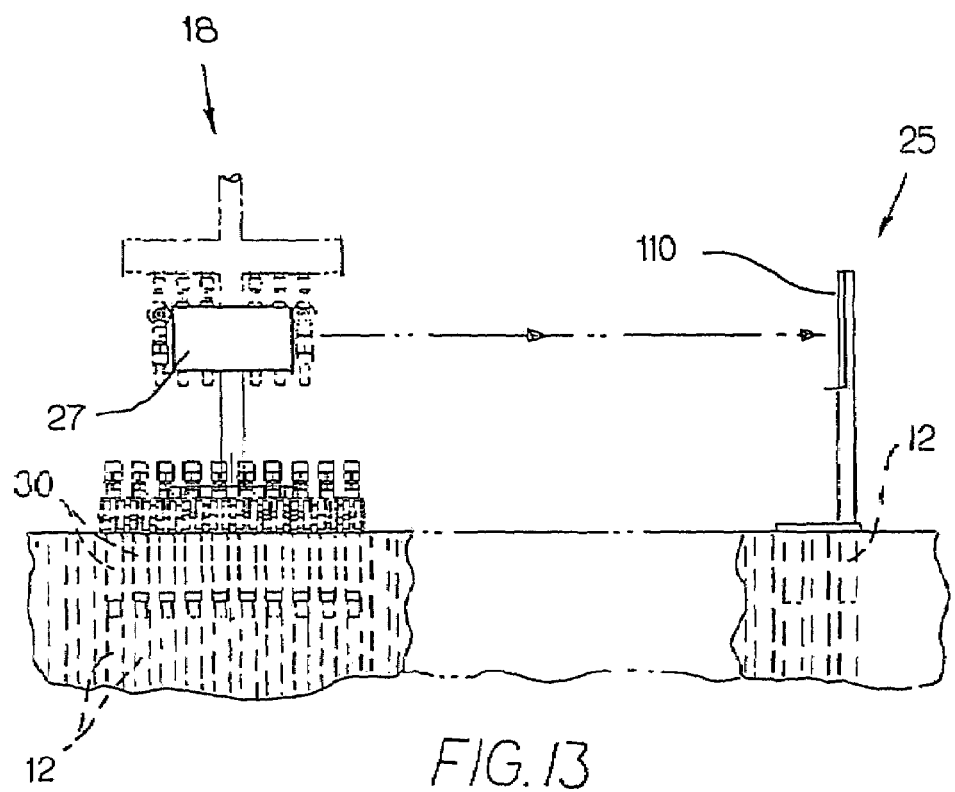
FIG. 13 is a broken-away schematic view of the upper portion of the reactor as the chemical reactor tubes are being blown down or measured by the device of FIG. 4.
Figure 15:
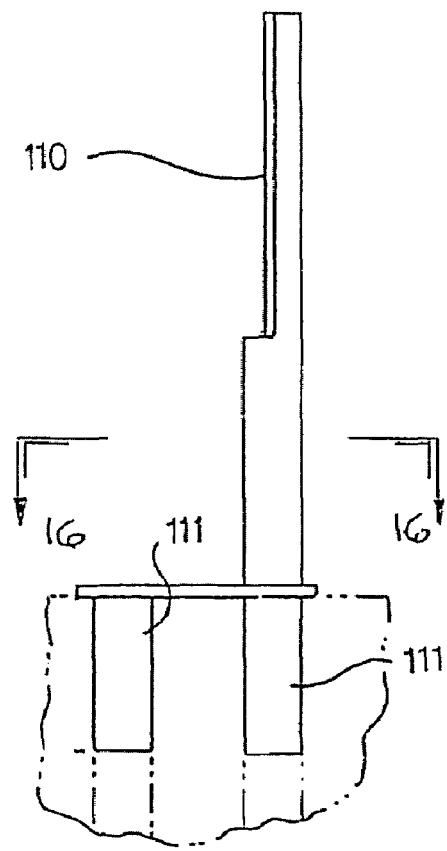
FIG. 15 is a side view of the target of FIG. 14.
Figure 16:
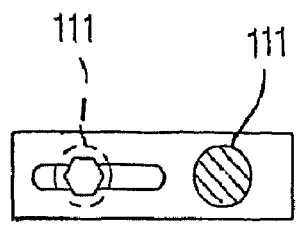
FIG. 16 is a view taken along the section 16-16 of FIG. 15.

FIG. 13 shows schematically the laser measurement device 27 on the wand 18 measuring a distance back to a target 25, which is mounted in the first tube 12 of the row of chemical reactor tubes 12 being measured. The laser measurement device 27 shines a light onto the reflector portion 110 of the target 25, and the light is reflected back to the device 27, establishing a distance measurement from the wand to the target, which is converted by the microcomputer 32 to a tube number. The software also permits the operator to put the flag into a different chemical reactor tube 12 other than the first tube and to instruct the central processor 32 to compensate accordingly, so that the central processor 32 always indicates the correct position of the wand 18. As shown in FIGS. 15 and 16, the target 25 has two legs 111, which fit into two adjacent chemical reactor tubes 12 in a row. One of the legs 111 preferably is mounted in a slot in order to permit adjustment of the spacing between the legs 111 to fit the spacing between chemical reactor tubes 12 in a particular reactor.

When the first tubes in a row are being measured, there is no reflector present, and the operator simply presses the "first tube" button 104 on the control panel to indicate that the first injector tube 30 on the wand 18 is being inserted into the first chemical reactor tube 12 in that row. When the operator removes the wand 18 from the first group of tubes, he inserts the reflector 110, and thereafter the display 92 on the control box 34 automatically indicates the tube position being measured based on the distance measurement from the laser measurement device 27. After the wand 18 has measured the end of a row, the display 92 automatically increases the row number in preparation for measuring the next row.

Figure 17:
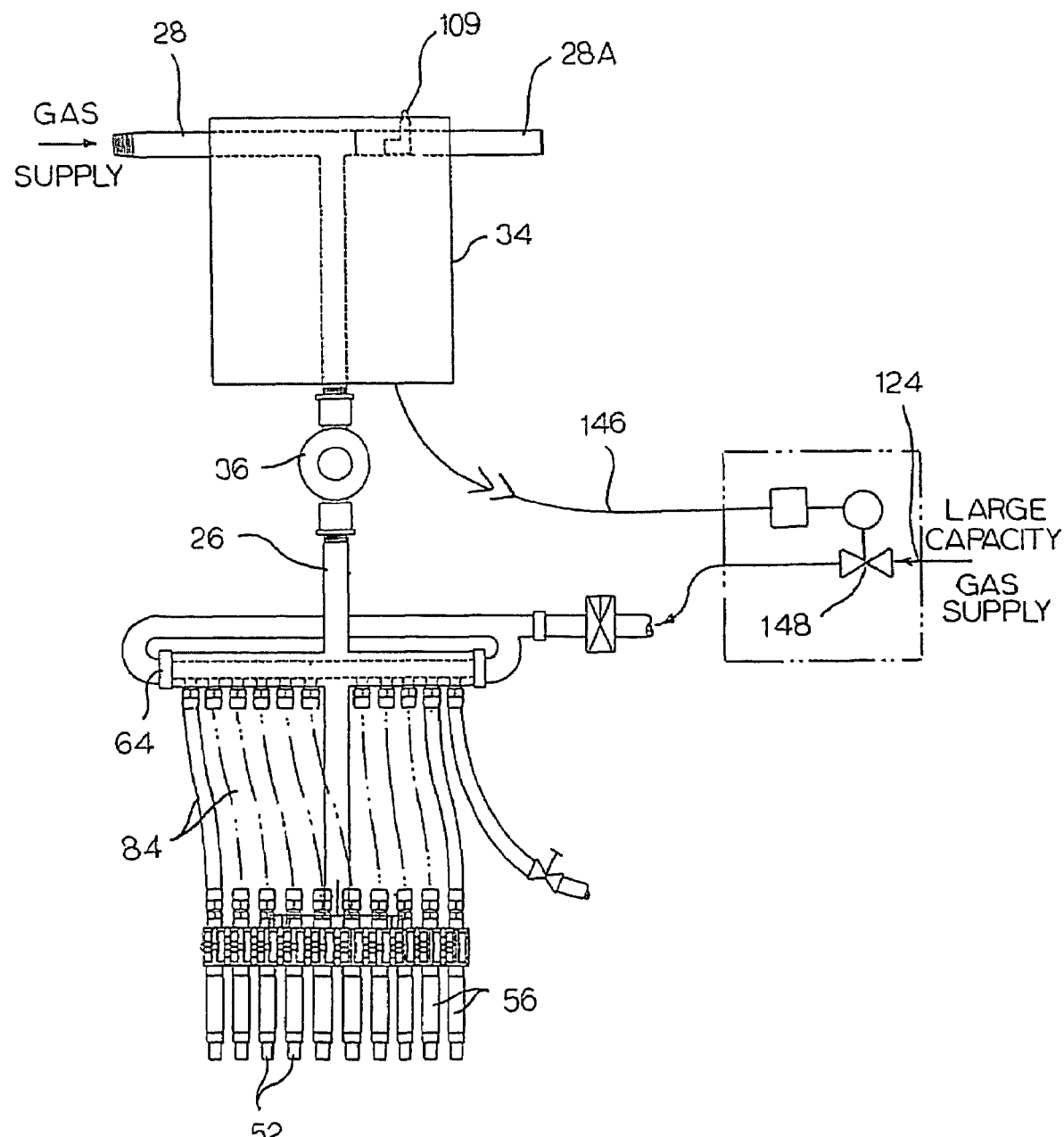
FIG. 17 is a schematic front view of the device of FIG. 4 after it has been reconfigured for blowdown.

FIG. 17 shows a wand 18 that has been reconfigured for use in blowing down the chemical reactor tubes 12. (While it is possible to use the wand 18 in its initial configuration to blow down tubes, the flow control devices 66 may prevent a high enough volume of gas from flowing through to be effective for blowing down the chemical reactor tubes 12 to remove dust. In that case, this reconfiguration may be used.) While there is still a gas inlet at the handle 28 in order to inflate the sleeves 56, anew gas inlet 124 has been provided to supply high volume gas for blowdown. This new gas inlet 124 feeds the main manifold 64, but the flow control devices 66 have been removed from the line, so that the gas simply flows straight through the main manifold 64 and through the lines 84, through the internal paths 54 of the tubes 52, and into the chemical reactor tubes 12. This permits a high volume of gas to be supplied into the chemical reactor tubes 12 to blow them down, removing dust. The operator may choose not to take pressure measurements during the blow-down operation, or the wand may be configured not to take pressure measurements during blow-down, if desired. However, the display 92 on the control panel of FIG. 11 will show which chemical reactor tubes 12 are being blown down, and the data may be transmitted to the laptop computer 22, indicating which tubes are being blown down, which wand 18 is being used, and the time and date of the procedure. The visual display 92 then will show the chemical reactor tubes 12 that have been blown down by indicating those tubes in a special color. This provides quality control, so the plant engineer can confirm that the tubes actually have been blown down.

While the wand 18 can be converted back and forth from the measurement mode to the blowdown mode, with the configurations shown here, it takes time to make the conversion. Therefore, it may be preferable simply to provide two different types of wands-one for taking measurements and one for blowdown. Alternatively, a valving arrangement may be provided to permit conversion from one mode to the other simply by opening and closing valves to open and close the different pathways that are used for the different operations, preferably bypassing the flow control devices 66 and closing the flow through the measurement tubes 72 during the blow down operation. Or, if sufficient gas flow can be achieved in the normal measurement arrangement to accomplish effective blowdown, then the original configuration of the wand may be used, and the wand's central processor 32 may simply provide for a delay in taking measurements, so that the test gas is first used for blowdown and then for taking measurements.

In the blowdown mode of FIG. 17, the control box 34 continues to function, using the laser measurement device 27 and target 25 to determine the chemical reactor tubes 12 that are being blown down and sending that information to the remote computer 22.

Figure 8A:
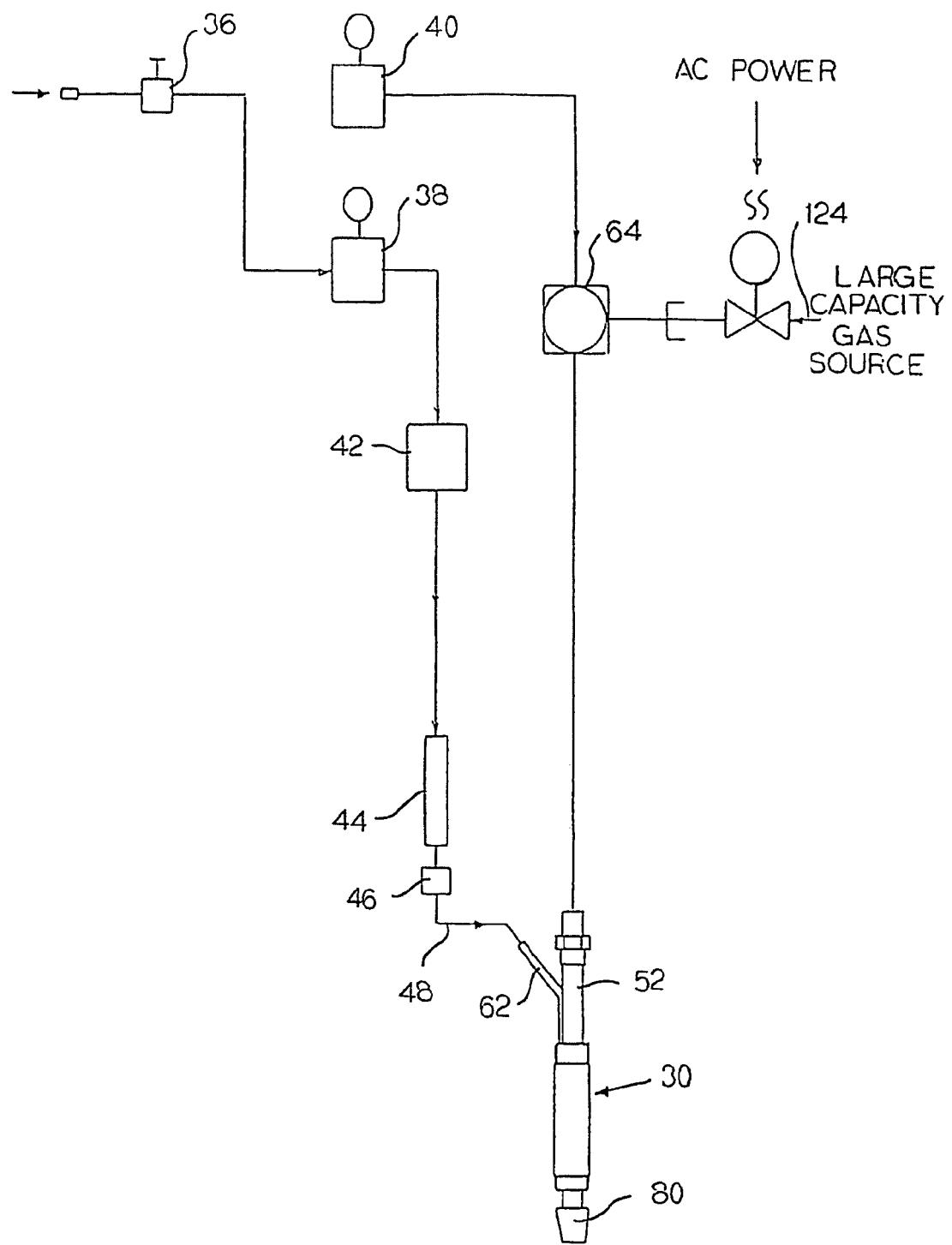
FIG. 8A is a schematic gas flow diagram for the device of FIG. 4 after it has been reconfigured for blowing down the chemical reactor tubes.

FIG. 8A shows the gas flow arrangement for the blowdown mode of FIG. 17. In that arrangement, the inflation gas route is the same as in the measurement mode. However, instead of the regular test gas route, the test gas used for blowdown simply goes through a valve, and then through the main manifold 64 to all the tubular members 52.

Figure 18:
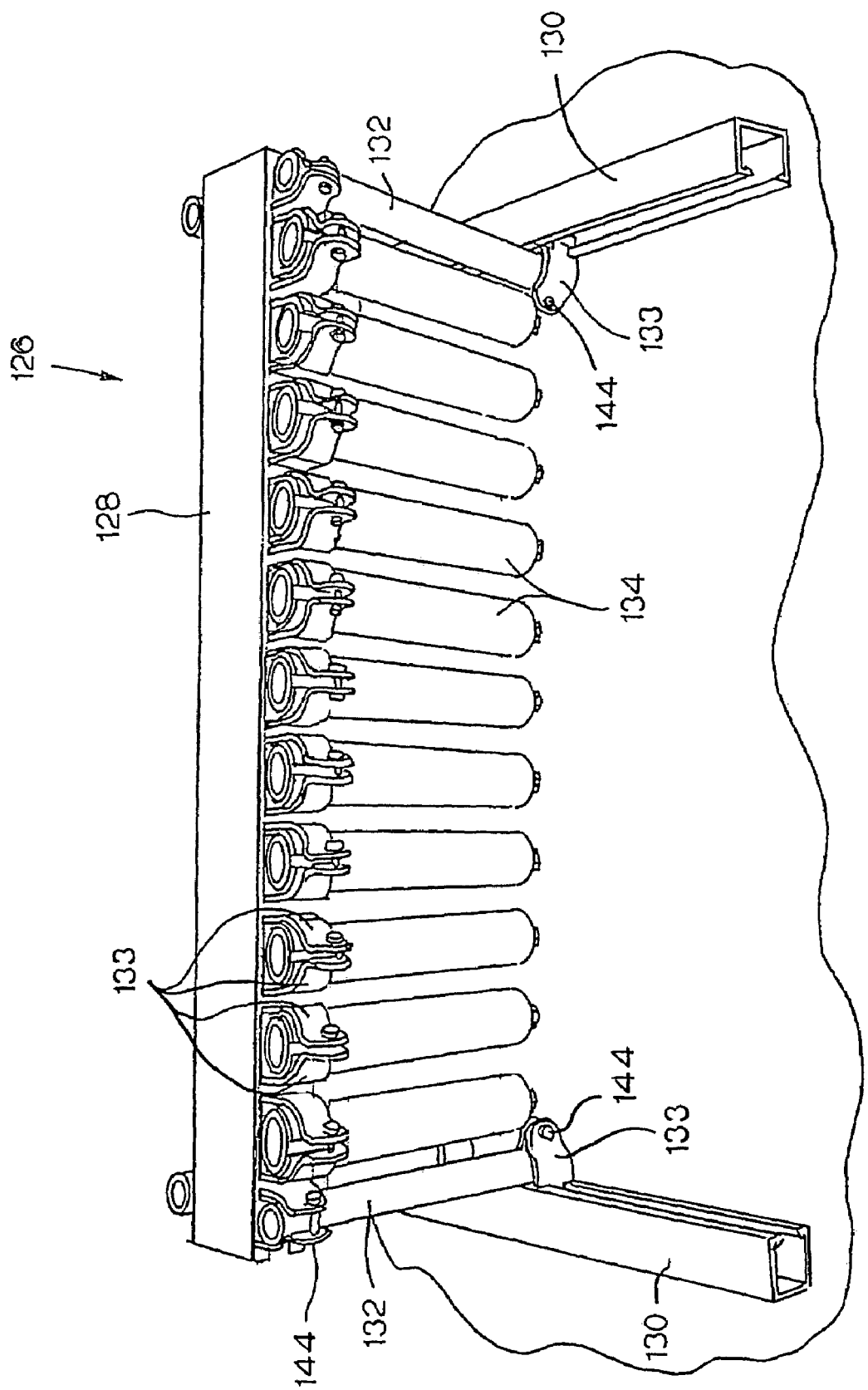
FIG. 18 is a perspective view of a calibration fixture for use with the device of FIG. 4.
Figure 19:
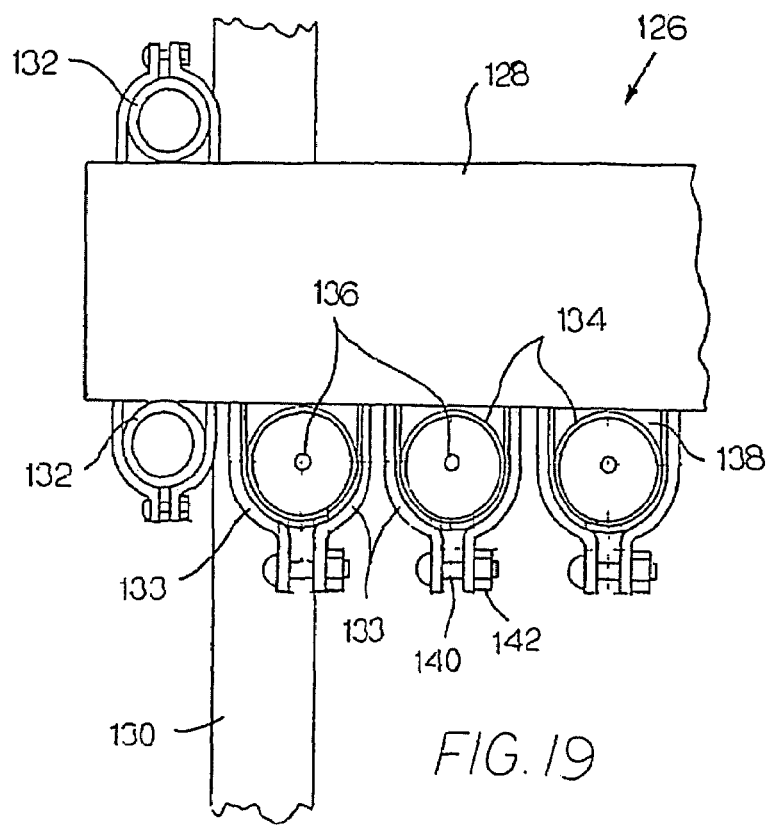
FIG. 19 is a broken-away top view of the calibration fixture of FIG. 18.
Figure 20:
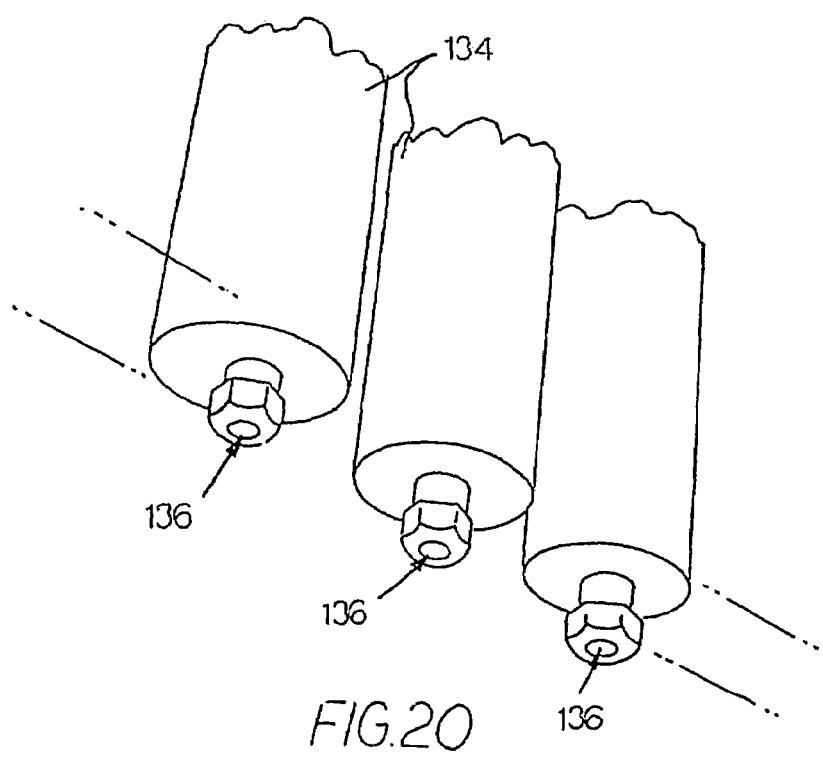
FIG. 20 is a broken-away bottom perspective view of a portion of the calibration fixture of FIG. 18.

FIGS. 18-20 show a test stand 126 used to calibrate the wand 18 for taking back pressure measurements. The stand 126 includes a frame member 128, which is supported on base frame members 130 by means of uprights 132. Several calibration tubes 134 are mounted on the frame member 128.

Figure 18A:
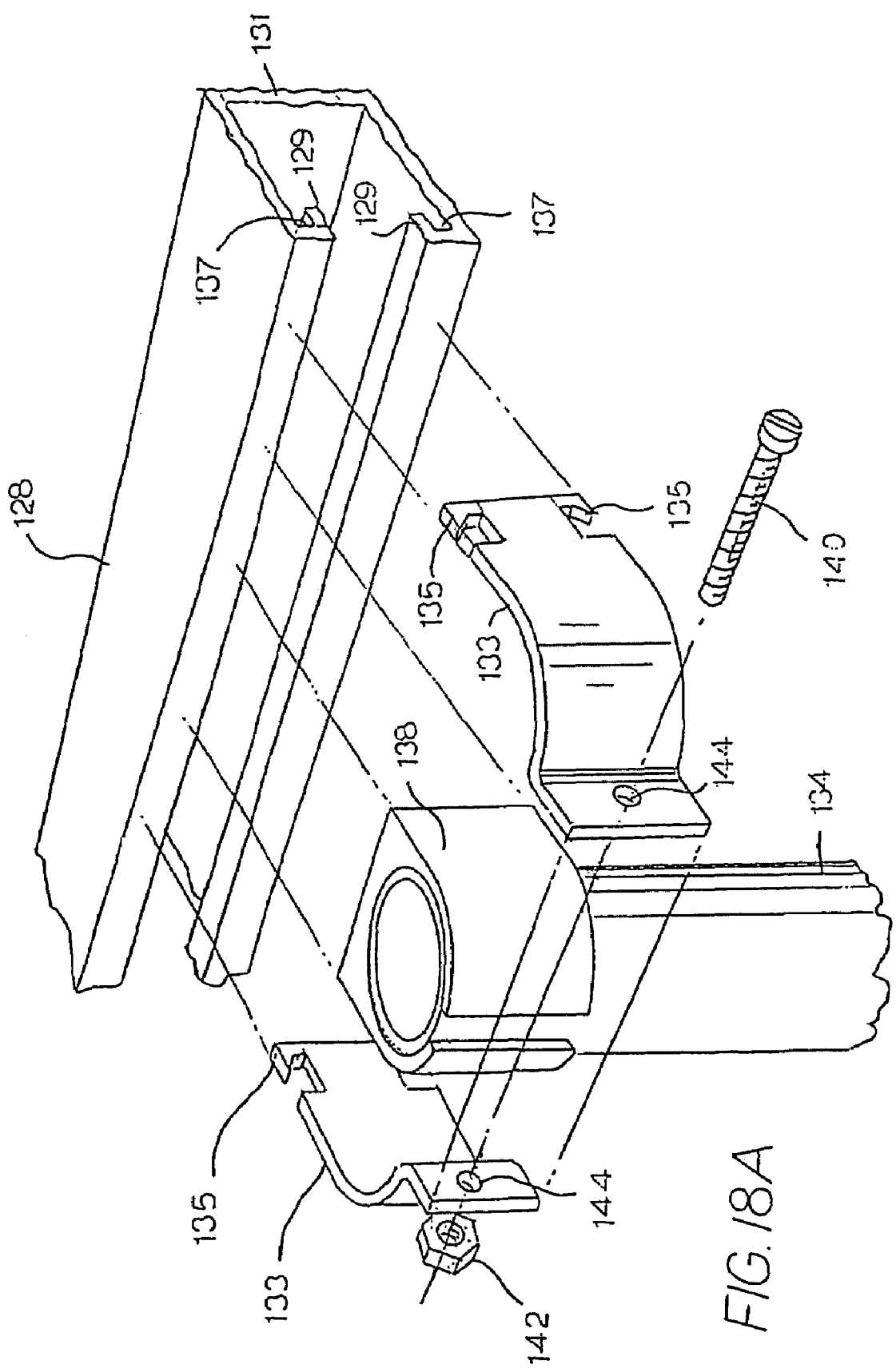
FIG. 18A is an exploded perspective view showing how the tubes of the calibration fixture of FIG. 18 are mounted on the frame, and this is the same mounting arrangement used for the tubes on the wand of FIG. 4.

As shown in FIG. 18A, the frame member 128 has a substantially U-shaped cross-section and includes lips 129 that project inwardly toward the base 131 of the U. Straps 133 have T-shaped ends, including hooked portions 135, which fit into the recesses 137 formed in the frame member 128. The straps 133 preferably are assembled onto, the frame member 128 by sliding them in from the end, and their shape, in cooperation with the shape of the frame member 128, restricts their movement relative to the frame member to linear movement along the frame member 128. A plastic end piece 138 is placed over the end of the calibration tube 134, and the straps 133 are clamped together around the end piece 138 and calibration tube 134 by means of bolts 140 and nuts 142, with the bolts 140 extending through holes 144 in the straps 133. This mounting arrangement allows the position of the calibration tube 134 to be adjusted along the length of the frame member 128 by sliding the straps 133 linearly along the frame and then to be fixed in place once the bolts 140 are tightened.

The uprights 132 are secured to the frame members 128, 130 in the same manner that the calibration tubes 134 are mounted onto the frame member 128, and the injector tubes 30 are secured onto the frame 50 of the wand 18 in the same manner as well. This permits adjustment of the positions of the injector tubes 30 along the frame members, and it permits different sizes of injector tubes 30 to be used on the same frame member 50. In this manner, the wand 18 can be reconfigured for measuring different reactors, having different tube diameters and different tube spacings.

Each of the calibration tubes 134 is closed at the bottom, except for a precision orifice 136 (see FIG. 20), which imitates the effect of the packing in the open-ended chemical reactor tubes 12. In order to calibrate the wand 18, the injector tubes 30 are inserted into the calibration tubes 134, gas is sent through the inflation path to seal the injector tubes 30 against the inside of the calibration tubes 134, and then gas is sent through the test path, and aback pressure reading is taken for each chemical reactor tube 12. The central processor 32 then generates correction factors as needed for each injector tube 30 in order to correct for any variations in the measurements, and these correction factors are used by the central processor 32 as the chemical reactor tubes 12 in a reactor are measured, in order to standardize the measurements from one injector tube 30 to another.

Figure 22:
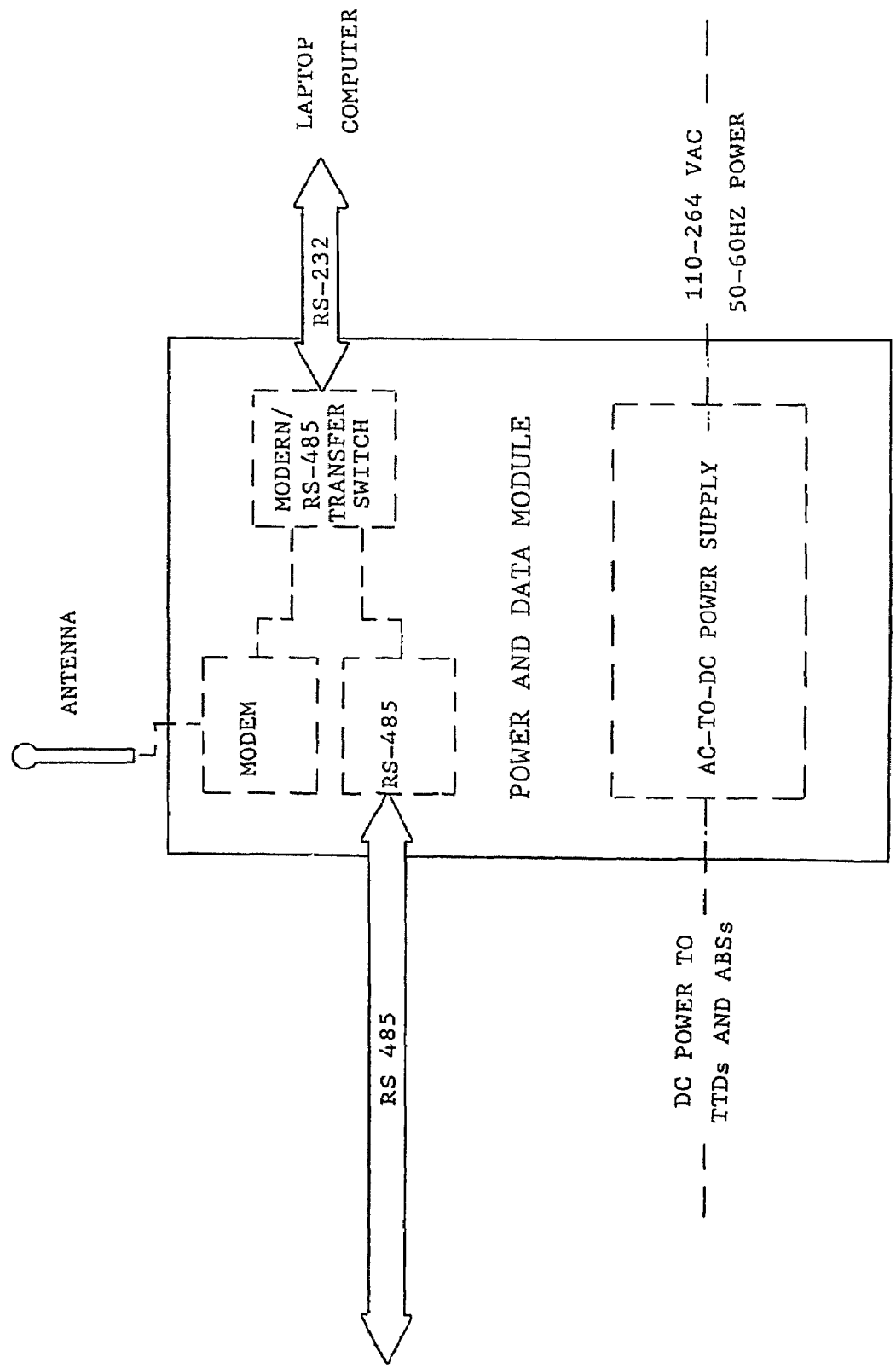
FIG. 22 is an electrical schematic of the power and data module portion of FIG. 21.

FIGS. 21 and 22 are an electrical schematic of the wand 18, showing the inputs and outputs to and from the central processor 32, which have already been described. There is a direct current power connection to the control box 34 of the wand 18, which may come from the remote power and data module 24 or from another power source. Measurements taken by the wand 18 may be transmitted through a modem and antenna 37 on the wand 18 to the antenna on the remote power and data module 24, or they may be transmitted through another means, as discussed earlier. Of course, this arrangement also permits the wand 18 to receive instructions or data from a remote source as well. The power and data module 24 communicates with the laptop computer 22. Alternatively, the data may simply be stored in the wand 18 and later downloaded to the remote computer 22.

Figure 23:
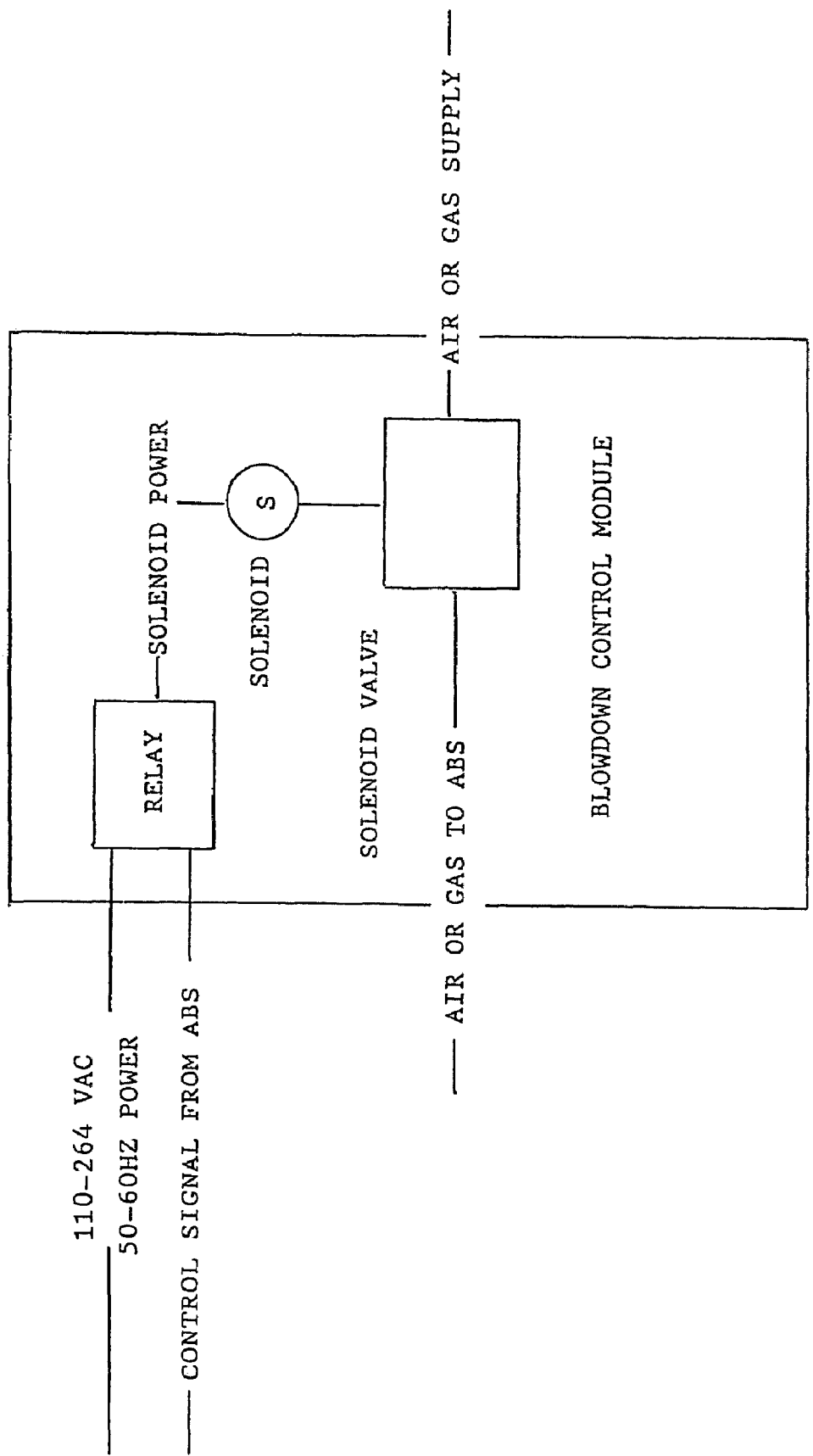
FIG. 23 is an electrical schematic of the blowdown control module of FIG. 17.

FIG. 23 shows the additional controls that are added for the blowdown mode as shown in FIG. 17. These controls take their power from the main control box 34 for the wand 18 through a power cord 146, and the valve 148 which opens a gas path from the inlet 124 to the main manifold 64 is only opened after the seals 56 are inflated.

In a typical setting, the wand 18 (or several wands 18) would be prepared with injector tubes 30, 30A having the correct diameters and spacings for the reactor to be measured. The configuration of the reactor, including the locations of the chemical reactor tubes 12 would be loaded into the wand central processor 32 and into the laptop computer 22. Then, the wands 18, power and data module 24, laptop computer 22, and calibration or test stand 126 would be transported to the site.

If blowdown is to be done first, then the wands 18 may be configured for blowdown, or special blowdown wands may be used if needed. The workers would then go along the plate 11, blowing down all the chemical reactor tubes 12. The workers would take their wands 18 to the end of a row, would use the toggle switch 108 if needed to make sure the display 92 is indicating the correct row, would insert the injector tubes 30 into the first group of chemical reactor tubes 12 in the row, and would push the "first tube" button 104, to indicate that the first tube is being measured. Then, the worker would push the "start" button 109 on the handle 28A. If the switch 82 is depressed, indicating that the wand 18 has been properly inserted into the chemical reactor tubes 12, then, when the "start" button 109 is pushed, the central processor 32 would open the solenoid valve 42 for the tube seals, inflating the sleeves 56 to seal against the inside of the chemical reactor tubes 12. The test gas would be flowing through the injector tubes 30 continuously. Once the first group of chemical reactor tubes 12 has been blown down, the worker would move to the next group of ten (or whatever number is provided on the wand) and would insert the target 25 into the first two tubes of the row so that the laser measuring device 27 could automatically measure the distance from the wand 18 to the target 25, thereby automatically determining which chemical reactor tubes 12 are being blown down. The central processor 32 would transmit this information electronically to the power and data module 24, telling it which wand 18 is being used, the time and date, and which chemical reactor tubes 12 are being blown down. (The identification of the worker who is using the wand 18 is expected to be in the set-up information that is input into the computer 22 before the test and therefore would hot have to be transmitted.) The power and data module 24 would, in turn, transmit this information to the laptop computer 22, so the plant engineer could see in real time on the computer screen the chemical reactor tubes 12 being blown down. If the wand 18 does not have to be reconfigured for blow-down, then the workers may perform the blow-down and the back-pressure measurement in one step, inserting the wand 18 into a bank of reactor tubes 12, blowing down the tubes, and then measuring the back pressure in the tubes before moving on to the next group of reactor tubes 12.

Before measurements are taken, the wands 18 would be configured for taking measurements and would be calibrated at the test stand 126. Again, each worker would take his wand 18 to the beginning of a row of chemical reactor tubes 12 to be measured and would insert the injector tubes 30 into the chemical reactor tubes 12. He would then use the row toggle switch 108 to make sure the correct row is showing on the display 92 and would then press the "first tube" button 104. Then, he would push the "start" button 109. If the switch 82 indicates that the injector tubes 30 are properly inserted into the chemical reactor tubes 12, the central processor 32 would open the solenoid valve 42 to inflate the seals oh the injector tubes 30. Then, the central processor 32 would open the multiplex valve 74, one channel at a time, permitting the pressure sensor 76 to measure the back pressures in the measurement tubes 72 one at a time, until the back pressure for all the injector tubes 30 has been measured, stored at the wand 18, and transmitted to the power and data module 24.

Once the first group of chemical reactor tubes 12 has been measured, the worker would move to the next group (of ten tubes in this arrangement) and would insert the target 25 in the first tube. Thereafter, the central processor 32 will automatically keep track of which chemical reactor tubes 12 are being measured, with the operator simply pressing the "start" button 109 each time a group of chemical reactor tubes 12 is to be measured, thereby causing the wand 18 to take the distance and pressure measurements and transmit the data for each chemical reactor tube 12 to the power and data module 24. If the worker comes to an obstacle or to the end of a row, he will put his tenth (or last) injector tube 30 into the last tube before the obstacle or the last tube at the end of the row, and may re-measure some of the chemical reactor tubes 12 that have already been measured.

If the worker comes to a chemical reactor tube 12 that cannot readily be reached by the whole wand 18, he may choose to use the umbilical wand 18A. This works in the same manner as the regular measurements, except that the worker would use the switch 98 to put the wand 18 into the manual mode and would use the toggle switches 106, 108 to be sure the correct tube row and tube number are being indicated. Then he would press the "start" switch 88 on the umbilical wand 18A, and, if the interlock switch 82A is closed, indicating that the injector tube 30 is fully inserted into the chemical reactor tube 12 to be tested, a measurement will be taken.

Adjustments for Changed Conditions

Since testing a reactor with as many as 30,000 chemical reactor tubes 12 can take a number of hours, even when using multiple wands 18 at the same time, changes in ambient conditions and in gas supply conditions during the test period can affect the pressure measurements. These changes may be corrected for based on the gas law pv=nrT. Changes in the ambient environment and in the gas supply that may be measured and adjusted for include: supply gas temperature, supply gas pressure, discharge gas temperature, barometric pressure, and ambient temperature. Also, chemical reactor tube 12 temperature changes may be considered and corrected for based on Darcy's equation. These pressure and temperature changes may be measured during the vessel testing period, and corrections to the pressure measurements may be made to assure that the results reflect a standard: condition of pressure, temperature and flow as initially calibrated, such that all pressure results correlate to the standard condition established when testing began. This is an especially important consideration if testing must be interrupted for an unrelated plant emergency or for inclement weather. Since these parameters generally change slowly over time, they can be measured with each and every use of the wand or at specified periods during the testing process. These measurements can be made on or off the wand 18 and applied to the raw pressure measurements or stored in the memory of the wand 18 or of the host computer 22 for later analysis.

Figure 24:
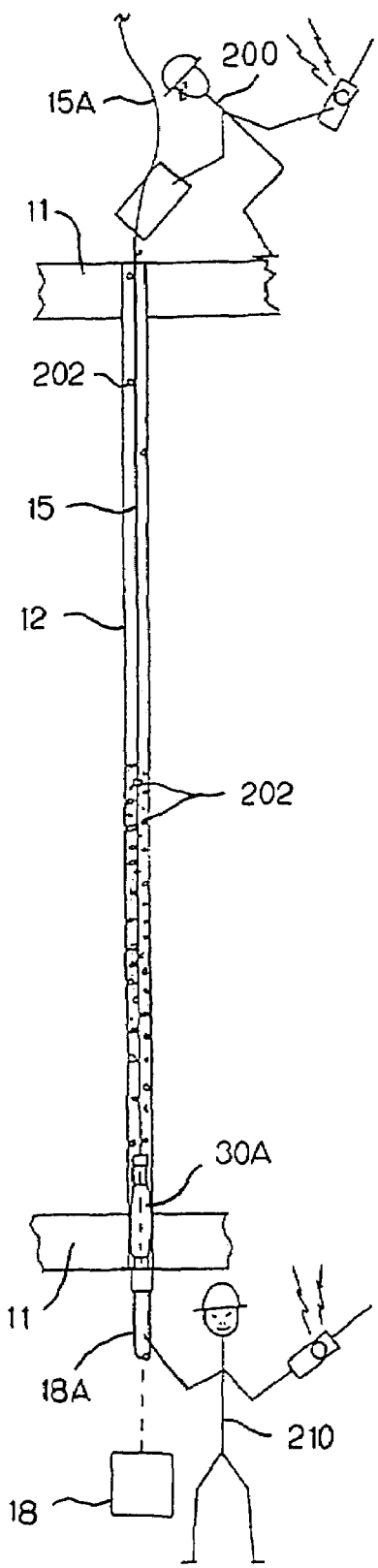
FIG. 24 is a schematic showing a method for loading a tube that includes a hollow sleeve housing several thermocouples, with the sleeve extending out the top of the tube.
Figure 25:
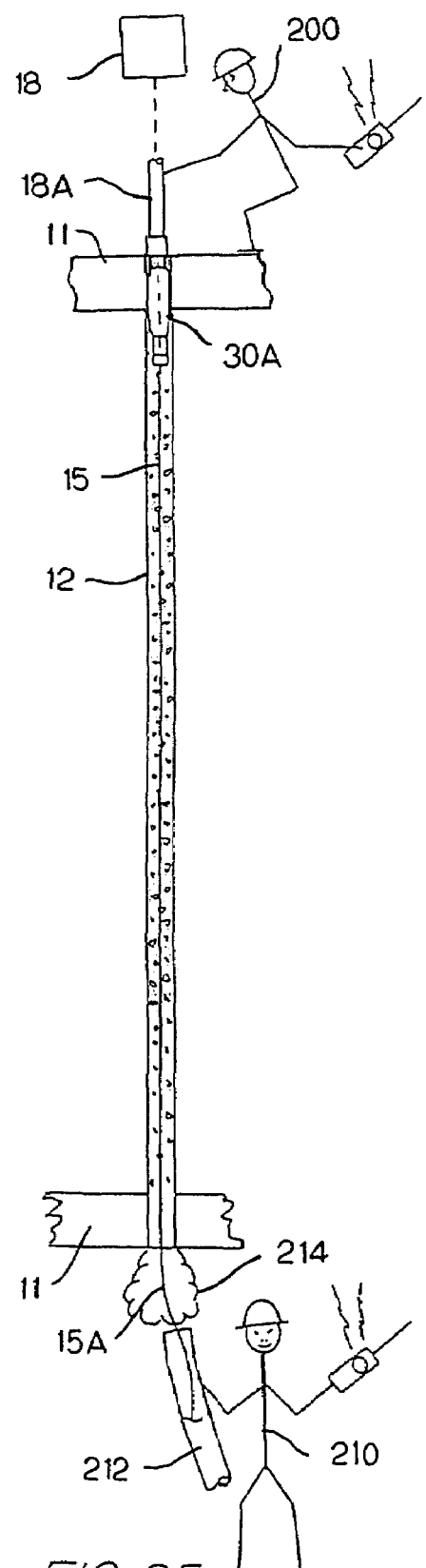
FIG. 25 is a schematic showing a method for blowing down a tube that includes a hollow sleeve housing several thermocouples, with the sleeve extending out the bottom of the tube.
Figure 26:
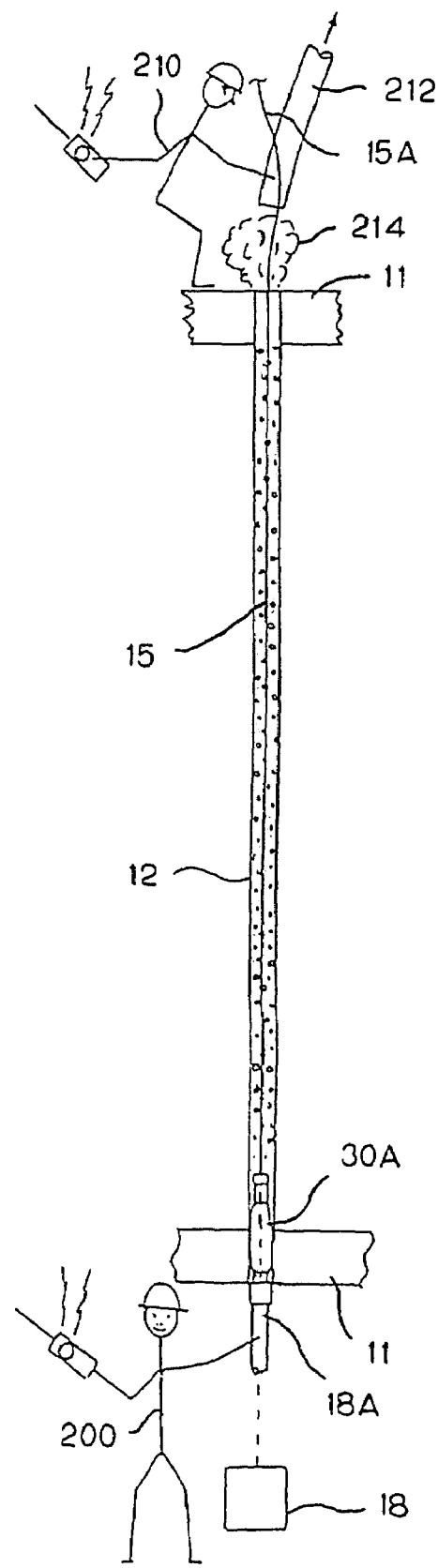
FIG. 26 is a schematic showing a method for blowing down a tube that includes a hollow sleeve extending out the top of the tube.

FIGS. 24-26 are schematics showing how the devices described above can be used for blowing down and measuring a tube 12 in which there is an axially-oriented obstruction, such as a hollow sleeve 15 containing a plurality of thermocouples, extending along the central axis of the tube 12. The thermocouples measure the temperature at various points inside the tube 12, and a portion 15A of the hollow sleeve projects out one end of the tube 12, either out the top, as shown in FIGS. 24 and 26, or out the bottom, as shown in FIG. 25, housing the leads from the thermocouples. Since the temperature measurements taken by the thermocouples are used to control the reactor, it is very important that the conditions in the tubes 12 containing the hollow sleeves 15 housing the thermocouples are as close as possible to the conditions in the regular tubes 12. However, it is more difficult to load catalyst into a tube 12 that contains an axial obstruction such as the hollow sleeve 15, because the sleeve 15 interferes with the ability of the catalyst pellets to pass into and along the tube 12.

The tube test device 18 may be used while loading a tube 12, especially a tube 12 containing a sleeve 15 or other obstruction, in order to help ensure that the tube 12 is properly loaded with catalyst. In those situations, the umbilical wand 18A is used at the end of the tube 12 opposite the projecting portion 15A of the hollow sleeve 15. Since the center of the injector tube 30A is hollow, the injector tube 30A easily fits over the end of the hollow sleeve 15 and seals against the inside of the tube 12 in the normal manner.

FIG. 24 shows a worker 200 loading catalyst 202 into the top of the tube 12, while another worker 210 is at the bottom of the tube 12, measuring the back pressure in the tube 12 during the loading process. The worker 210, who is taking the measurements using the umbilical 18A, may radio the worker 200, who is doing the loading, to let him know what the back pressure is as the catalyst is being loaded. The worker 200 who is loading the catalyst will regularly measure the distance from the upper plate 11 to the catalyst level in the tube 12 by some known means, such as by inserting a tape measure or a measuring stick down into the tube 12 until it abuts the catalyst 202. He then uses the back pressure reading to determine whether the catalyst 202 is properly loaded for that depth. This helps train the worker 200 to load the catalyst properly, and, if there is a bridging or other problem, the catalyst can be removed and the filling can be restarted at an early stage, as soon as the problem is detected, rather than waiting until the tube is completely filled and fails a test. Various measurements may be taken at various heights to ensure that the catalyst density is correct throughout the tube 12. While the workers 200, 210 are shown here using radios to talk with each other and to transmit the pressure readings verbally, it is understood that the pressure readings, as well as other information, may be transmitted directly from the tube test device 18 to another type of receiver such as a laptop computer 22, as described earlier.

If the projecting end 15A of the hollow sleeve 15 extends out the bottom of the tube 12, as shown in FIG. 25, then the person 210 who is taking the pressure measurements as well as the person 200 who is loading the catalyst 202 would be on top of the top plate 11, and they might in fact be the same person.

The umbilical wand 18A may also be used for blowing down a tube 12 containing a thermocouple 15, as shown in FIGS. 25 and 26. In this case, the umbilical wand 18A is preferably on a modified blowdown device, such as the device shown in FIG. 17. The modified device need not be equipped to take pressure measurements and may be equipped to permit the flow of gas at higher pressures than the original device.

As shown in FIG. 25, the worker 200, who is standing on the top plate 11, has inserted, the umbilical injector tube 30A into the top of the tube 12, surrounding the top end of the hollow sleeve 15 containing the thermocouples, and has sealed the injector tube 30A against the inside surface of the tube 12. He then blows air through the umbilical 18A and through the injector tube 30A to blow dust out the bottom of the tube 12. The worker 210 at the bottom of the tube 12 uses a vacuum hose 212 to vacuum out the dust 214. Typically, the dust would be allowed to accumulate at the bottom, and then the worker 210 would come along and vacuum it up after the blowdown is completed.

FIG. 26 shows the same procedure as FIG. 25, except that, since the projection 15A from the hollow sleeve 15 housing the thermocouples extends out the top of the tube, the positions of the workers are reversed. The worker 200, who is blowing down the tube 12 is at the bottom of the tube 12, and the worker 210, who is vacuuming out the dust 214, is on top of the top plate 11. In this case, the vacuuming is done simultaneously with the blowdown in order to prevent the dust 214 from falling into other tubes and contaminating them.

The embodiments described above are intended simply as examples of devices and methods in accordance with the present invention. It will be obvious to those skilled in the art that a wide variety of modifications may be made to the embodiments described above without departing from the scope of the present, invention.

The invention claimed is:

1. A device for measuring back pressure in open-ended chemical reactor tubes, comprising:
   a rigid wand body having upper and lower ends and including a frame member at said lower end;
   a plurality of hollow tube bodies mounted on said frame member,
   a tubular elastic sleeve mounted over the outer surface of each of said hollow tube bodies, each tubular elastic sleeve having a top and a bottom;
   top and bottom ferrules clamping the top and bottom of each tubular elastic sleeve against its respective hollow tube body;
   an inflation gas path extending to the interior of each tubular elastic sleeve for inflating the respective sleeve;
   a plurality of paths for providing controlled gas flow through said plurality of hollow tube bodies; and
   a pressure sensor in fluid communication with at least one of said hollow tube bodies.

2. A device for measuring back pressure in open-ended chemical reactor tubes as recited in claim 1, wherein the top ferrule extends below the frame member.

3. A device for measuring back pressure in open-ended chemical reactor tubes as recited in claim 1, and further including means for adjusting the spacing between the plurality of hollow tube bodies and for fixing the positions of the plurality of hollow tube bodies relative to said rigid wand body.

4. A device for measuring back pressure in open-ended chemical reactor tubes as recited in claim 3, and further comprising an additional hollow tube body mounted on said wand by a flexible mounting means which permits its insertion into a reactor tube independently of said plurality of hollow tube bodies; an additional tubular elastic sleeve mounted over said additional hollow tube body; an additional inflation path extending to the interior of said additional tubular elastic sleeve for inflating said sleeve; and an additional path for providing controlled gas flow through said additional hollow tube body.

5. A device for measuring back pressure in open-ended chemical reactor tubes as recited in claim 1; wherein each of said hollow tube bodies has an outer surface and an inner surface, said outer surface defining a recess, and said inner surface defining an internal fluid path, wherein said inflation gas path includes an inflation tube lying within the recess between one of said ferrules and the hollow tube body.

* * * * *

UNITED STATES PATENT AND TRADEMARK OFFICE
CERTIFICATE OF CORRECTION

PATENT NO. : 7,673,496 B2  Page 1 of 1
APPLICATION NO. : 12/201278
DATED : March 9, 2010
INVENTOR(S) : Clifford L. Johns et al.

It is certified that error appears in the above-identified patent and that said Letters Patent is hereby corrected as shown below:

Column 4, line 63, delete "30a" and insert therefor --30--a--.
Column 6, line 58, delete "arranged;linearly" and insert therefor --arranged linearly--.
Column 8, line 52, delete "want" and insert therefor --wand--.
Column 10, line 15, delete "oh" and insert therefor --on--.
Column 10, line 28, delete "may be;" and insert therefor --may be--.
Column 11, line 47, delete "anew" and insert therefor --a new--.
Column 12, line 40, delete "onto, the frame" and insert therefor --onto the frame--.
Column 14, line 5, delete "would hot have" and insert therefor --would not have--.
Column 15, line 8, delete "standard: condition" and insert therefor --standard condition--.

Signed and Sealed this

Eleventh Day of May, 2010

David J. Kappos
*Director of the United States Patent and Trademark Office*